(12) United States Patent
Crossman

(10) Patent No.: US 8,137,342 B2
(45) Date of Patent: Mar. 20, 2012

(54) CIRCUMFERENTIAL ABLATION GUIDE WIRE SYSTEM AND RELATED METHOD OF USING THE SAME

(76) Inventor: Arthur W. Crossman, Daytona Beach, FL (US)

( * ) Notice: Subject to any disclaimer, the term of this patent is extended or adjusted under 35 U.S.C. 154(b) by 1145 days.

(21) Appl. No.: 11/919,718

(22) PCT Filed: Dec. 21, 2006

(86) PCT No.: PCT/US2006/049097
§ 371 (c)(1),
(2), (4) Date: Oct. 31, 2007

(87) PCT Pub. No.: WO2007/076045
PCT Pub. Date: Jul. 5, 2007

(65) Prior Publication Data
US 2009/0093801 A1    Apr. 9, 2009

Related U.S. Application Data

(60) Provisional application No. 60/753,804, filed on Dec. 24, 2005, provisional application No. 60/780,627, filed on Mar. 9, 2006, provisional application No. 60/800,522, filed on May 15, 2006.

(51) Int. Cl.
*A61B 18/18* (2006.01)
(52) U.S. Cl. .............. 606/41; 606/21; 606/33
(58) Field of Classification Search .......... 606/21–42
See application file for complete search history.

(56) References Cited

U.S. PATENT DOCUMENTS

| | | |
|---|---|---|
| 3,983,879 A | 10/1976 | Todd |
| 4,273,128 A | 6/1981 | Lary |
| 4,531,943 A | 7/1985 | Van Tassel |
| 4,543,087 A | 9/1985 | Sommercorn |
| 4,738,666 A | 4/1988 | Fuqua |
| 4,770,653 A | 9/1988 | Shturman |
| 4,927,412 A | 5/1990 | Menasche |
| 5,002,532 A | 3/1991 | Gaiser |
| 5,021,043 A | 6/1991 | Becker |
| 5,084,010 A | 1/1992 | Plaia |
| 5,087,247 A | 2/1992 | Horn |
| 5,169,386 A | 12/1992 | Becker |
| 5,213,576 A | 5/1993 | Abiuso |
| 5,234,416 A | 8/1993 | Macaulay |
| 5,290,310 A | 3/1994 | Makower |
| 5,395,333 A | 3/1995 | Brill |
| 5,505,730 A | 4/1996 | Edwards |
| 5,613,950 A | 3/1997 | Yoon |
| 5,617,854 A | 4/1997 | Munsif |

(Continued)

FOREIGN PATENT DOCUMENTS
WO    WO 2006/044670    4/2006
(Continued)

*Primary Examiner* — Linda Dvorak
*Assistant Examiner* — Amanda Scott
(74) *Attorney, Agent, or Firm* — Robert J. Decker

(57) ABSTRACT

Device and method significantly that improves the safety and procedural success of the existing art by being able to be less traumatic to vascular tissue, improving atrial contact with the ablation surface, improving positioning and geometrical precision of the ablation pattern, improving steerability and deliverability of the ablation device and by improving localization and geometric precision of the ablation device. The risk of pulmonary vein fibrosis/stenosis will also be substantially lowered. Finally, expansion of the eligible atrial fibrillation population will inherently increase due to the improved components and methods of the present invention.

62 Claims, 18 Drawing Sheets

U.S. PATENT DOCUMENTS

| | | |
|---|---|---|
| 5,687,723 A | 11/1997 | Avitall |
| 5,695,457 A | 12/1997 | St. Goar |
| 5,775,327 A | 7/1998 | Randolph |
| 5,807,318 A | 9/1998 | St. Goar |
| 5,814,016 A | 9/1998 | Valley |
| 5,833,650 A | 11/1998 | Imran |
| 5,868,703 A | 2/1999 | Bertolero |
| 6,013,072 A | 1/2000 | Winston |
| 6,086,581 A | 7/2000 | Reynolds |
| 6,126,649 A | 10/2000 | VanTassel |
| 6,206,852 B1 | 3/2001 | Lee |
| 6,270,480 B1 | 8/2001 | Dorr |
| 6,290,697 B1 * | 9/2001 | Tu et al. ............................ 606/27 |
| 6,383,151 B1 | 5/2002 | Diederich |
| 6,447,462 B1 | 9/2002 | Wallace |
| 6,491,710 B2 | 12/2002 | Satake |
| 6,503,247 B2 | 1/2003 | Swartz |
| 6,512,957 B1 | 1/2003 | Witte |
| 6,629,987 B1 | 10/2003 | Gambale |
| 6,632,223 B1 | 10/2003 | Keane |
| 6,638,247 B1 | 10/2003 | Selmon |
| 6,663,621 B1 | 12/2003 | Winston |
| 6,702,811 B2 | 3/2004 | Stewart |
| 6,723,082 B1 | 4/2004 | Payne |
| 6,730,063 B2 | 5/2004 | Delaney |
| 6,746,462 B1 | 6/2004 | Selmon |
| 6,758,847 B2 | 7/2004 | Maquire |
| 6,770,059 B1 | 8/2004 | Spinks |
| 6,773,447 B2 | 8/2004 | Laguna |
| 6,800,065 B2 | 10/2004 | Duane et al. |
| 6,808,524 B2 * | 10/2004 | Lopath et al. .................... 606/27 |
| 6,811,544 B2 | 11/2004 | Schaer |
| 6,926,714 B1 | 8/2005 | Sra |
| 6,936,056 B2 | 8/2005 | Nash |
| 7,691,081 B2 | 4/2010 | Crossman |
| 2001/0023334 A1 | 9/2001 | St. Goar |
| 2003/0065307 A1* | 4/2003 | Lesh ............................ 604/509 |
| 2003/0088211 A1 | 5/2003 | Anderson |
| 2003/0130610 A1 | 7/2003 | Mager |
| 2003/0163156 A1 | 8/2003 | Hebert |
| 2003/0195510 A1* | 10/2003 | Schaer ............................ 606/41 |
| 2004/0158141 A1 | 8/2004 | Scheib |
| 2004/0162519 A1 | 8/2004 | Helkowski |
| 2005/0010095 A1* | 1/2005 | Stewart et al. ................. 600/374 |
| 2005/0165391 A1* | 7/2005 | Maguire et al. ................. 606/41 |
| 2007/0112369 A1 | 5/2007 | Crossman |
| 2008/0249420 A1 | 10/2008 | Crossman |

FOREIGN PATENT DOCUMENTS

| | | |
|---|---|---|
| WO | WO 2007/053777 | 5/2007 |
| WO | WO 2007/076045 | 7/2007 |

* cited by examiner

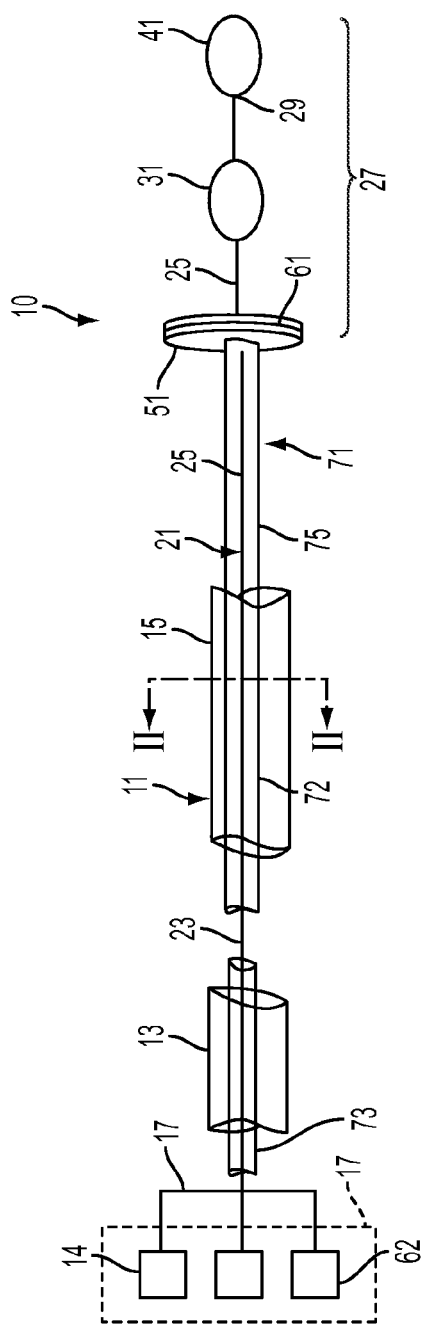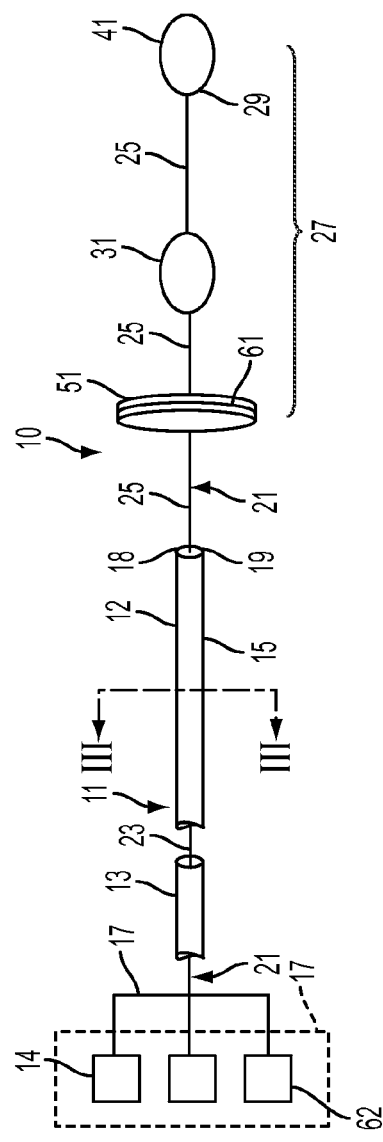
FIG. 1A
FIG. 1B

CIRCUMFERENTIAL ABLATION GUIDE WIRE SYSTEM AND RELATED METHOD OF USING THE SAME

RELATED APPLICATIONS

The present patent application is a national stage filing of International Application No. PCT/US2006/049097, filed on Dec. 21, 2006, which claims benefit under 35 U.S.C. Section 119(e) from U.S. Provisional Application Ser. No. 60/753,804, filed Dec. 24, 2005, entitled "Circumferential Ablation Guide Wire System and Related Method of Using the Same," No. 60/780,627, filed Mar. 9, 2006, entitled "Circumferential Ablation Guide Wire System and Related Method of Using the Same," and No. 60/,800,522, filed May 15, 2006, entitled "Circumferential Ablation Guide Wire System and Related Method of Using the Same," the entire disclosures of which are hereby incorporated by reference herein.

BACKGROUND OF THE INVENTION

Atrial fibrillation is a very common arrhythmia which accounts for a substantial amount of morbidity, mortality and costs. Specifically it can lead to death, stroke, transient ischemic attack, syncope, congestive heart failure, myocardial ischemia, myocardial infarction, palpitations, malignant arrhythmia, and altered mental status. Treatment options have traditionally consisted of anticoagulation, heart rate control and heart rhythm control. Significant morbidity and mortality also results from treatment. Anticoagulation can lead to hemorrhagic stroke and bleeding. Anticoagulation with coumadin can be very labor intensive, resource demanding, inconvenient secondary to the need for frequent International Normalized Ratio (INR) checks and very susceptible to drug interaction leading to over or under anticoagulation and their respective sequlea of bleeding and stroke. Heart rate control commonly leads to drug side effects from beta blockers, calcium channel blockers and dioxin. Potentially ensuing bradyarrythmia may require a permanent pacemaker. Antiarrythmic medication can cause sudden death, malignant arrhythmia and multiple toxicities such as liver, thyroid, lens and pulmonary toxicity with amiodarone and lupus like syndrome with procainamide. Costs and polypharmacy are additional burdens of medical management of atrial fibrillation. Mechanical and chemical cardioversions can be risky and require additional procedures with their own inherent risks such as trans-esophageal echocardiography with conscience sedation and/or anesthesia.

Recently atrial fibrillation ablation procedures have introduced a long sought after permanent solution to the common and cumbersome management issues associated with atrial fibrillation. However, the nascent developments of atrial fibrillation ablation procedures have met their own obstacles. Namely, low success rates, applicability to low risk patient populations, risk of cardiovascular trauma and risk of early of latent pulmonary vein fibrosis and thus stenosis. Certainly much room exists to improve upon the safety, efficacy and inclusion of higher risk patient populations in regards to existing atrial fibrillation ablation catheter based systems.

There is therefore a need in the art for a more effective and safer method of wire positioning and tissue ablation of the left atrium. The various aspects of the embodiments of the present invention overcome and/or mitigate the aforementioned problems.

BRIEF SUMMARY OF INVENTION

Atrial fibrillation is a highly prevalent arrhythmia associated with significant morbidity, mortality and cost. Traditional medical management and mechanical cardioversion has resulted in a suboptimal solution to this common arrhythmia. Atrial fibrillation ablation has offered a long sought after solution to this vexing problem. Unfortunately excitement for contemporary catheter ablation techniques and equipment have been blunted by low success rates in a low risk patient populations as well resulting complications such as pulmonary vein fibrosis/stenosis and vascular trauma.

The various embodiments of the present invention device and method significantly improves the safety and procedural success of the existing art by being able to be less traumatic to vascular tissue, improving atrial contact with the ablation surface, improving positioning and geometrical precision of the ablation pattern, improving steerability and deliverability of the ablation device and by improving localization and geometric precision of the ablation device. The risk of pulmonary vein fibrosis/stenosis will also be substantially lowered. Finally, expansion of the eligible atrial fibrillation population will inherently increase due to the improved components and methods of the present invention.

An aspect of various embodiments of the present invention provides a tissue ablation system and related method for treating atrial arrhythmia by ablating a circumferential region of tissue at a location where a pulmonary vein (PV) extends from an atrium of a heart of a subject. The system comprising: a guide catheter comprising a shaft having a proximal portion and a distal portion; a guide wire disposed in the guide catheter shaft having a proximal portion, distal portion and distal tip, wherein the guide wire is adapted to travel through the guide catheter to be inserted into the atrium; an interface member disposed on the guide wire; a first balloon disposed on the guidewire distally beyond the interface member, wherein the first balloon is adapted to center or align the guide wire in the pulmonary vein (PV) and/or its pulmonary vein ostium (PVO) so that the interface member is coaxially aligned with the pulmonary vein ostium (PVO) to provide optimal coaxial alignment with the pulmonary vein ostium (PVO); and an actuator element disposed on the interface member. The interface member may be positioned to center and/or align the guide wire, the interface member and/or actuator element in the pulmonary vein (PV) and/or it's pulmonary vein ostium (PVO) so that the interface member and/or actuator element is coaxially aligned with the pulmonary vein ostium (PVO) to provide optimal coaxial alignment with the pulmonary vein ostium (PVO).

Another aspect of various embodiments of the present invention may provide the interface member comprising a plurality of panels folded or collapsed over causing the interface member to be in a deflated or restricted state and unfolded or un-collapsed causing the interface member to be in an inflated or expanded state.

Another aspect of various embodiments of the present invention further comprise: a delivery catheter comprising a shaft having a proximal portion and a distal portion, wherein the delivery catheter travels coaxially through the guide catheter and the guide wire travels coaxially through the delivery catheter; a proximal hub slidably disposed on the delivery catheter at distal portion of the delivery catheter, wherein the distal hub having a plurality of proximal spokes attached to the proximal hub; and a distal hub slidably disposed on the delivery catheter and in contact with the proximal hub, wherein the distal hub having a plurality of distal spokes attached to the distal hub. Further, when a force is applied in a distal direction to the proximal hub the proximal hub is pushed as close to the distal hub as possible, or as desired, thereby causing the proximal and distal set of spokes to be deployed and flare outward relative to the longitudinal axis of the proximal hub and distal hub. Further yet, when a force is applied in a proximal direction to the proximal hub the proximal hub pulled away or slid away from the distal hub as much as possible, or as desired, thereby causing the proximal and distal set of spokes to be in a to collapse in a non-deployed state.

An aspect of various embodiments of the present invention provides a tissue ablation system and related method for treating atrial arrhythmia by ablating a circumferential region of tissue at a location where a pulmonary vein (PV) extends from an atrium of a heart of a subject. The system comprising: a guide catheter comprising a shaft having a proximal portion and a distal portion; a guide wire disposed in the guide catheter shaft having a proximal portion, distal portion and distal tip, wherein the guide wire adapted to travel through the guide catheter to be inserted into the atrium; an interface member disposed on the guide wire; a first balloon disposed on the guidewire distally beyond the interface member, wherein the first balloon comprises distal end, distal portion, proximal end and proximal portion; and an actuator element disposed on the interface member. Further, the non-compliant portion being located on the proximal portion of the first balloon, wherein the proximal portion having a desired/required radius that may vary along its continuum. Further yet, the non-compliance portion may be adapted to center or align the guide wire in the pulmonary vein (PV) and/or its pulmonary vein ostium (PVO) so that the interface member is coaxially aligned with the pulmonary vein ostium (PVO) to provide optimal coaxial alignment with the pulmonary vein ostium (PVO).

Another aspect of various embodiments of the present invention wherein may provide at least a portion of the proximal portion of the first balloon comprising a neck or flair.

These and other aspects of the disclosed technology and systems, along with their advantages and features, will be made more apparent from the description and drawings that follow.

BRIEF SUMMARY OF THE DRAWINGS

The foregoing and other objects, features and advantages of the present invention, as well as the invention itself, will be more fully understood from the following description of preferred embodiments, when read together with the accompanying drawings, in which:

FIG. 1(A) illustrates a schematic elevation view of an embodiment of the present invention ablation assembly with a catheter guide, delivery guide, guide wire and further comprising an interface member, ablation element, alignment/centering balloon and non-traumatic tip.

FIG. 1(B) illustrates the embodiment the ablation assembly FIG. 1(A) with one less catheter body.

FIG. 5(A) schematically illustrates the use of the tip balloon, interface member, centering/alignment balloon, and actuator element relative to the PV and/or PVO.

DETAILED DESCRIPTION OF THE INVENTION

Figure 2:
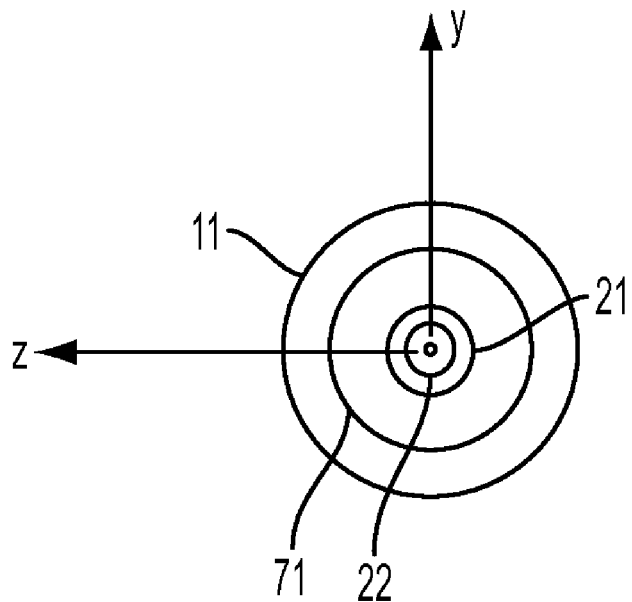
FIG. 2 illustrates a cross-section view II-II as shown in FIG. 1(A) of the ablation assembly.

Turning to FIG. 1(A), FIG. 1(A) illustrates a schematic elevation view of an embodiment of the present invention ablation assembly 10 including a delivery catheter 71 having a delivery catheter shaft 72 with a proximal portion 73, distal portion 75, and an operator device 17. The delivery catheter 71 travels coaxially through a guide catheter 11 having a catheter shaft 12 with a proximal portion 13 and distal portion 15. The delivery catheter 71 accommodates a guide wire 21 that coaxially travels through the delivery catheter 71 to be inserted into a left atrium (LA) of the heart (not shown), or at a location of the vasculature as required or desired. The guide wire 21 can be used to cross the septum itself (with or without the guide catheter and/or delivery catheter) or act as a positioning mechanism, which will be discussed in greater detail below. The guide wire 21 includes a proximal portion 23 and distal portion 25 of the guide wire 21, and a distal tip 29, centering/alignment balloon 31 (or inflatable compartment) that may be disposed at or proximal to the beginning of the distal extension 27 of the guide wire 25, as well as any portion of the distal extension 27. The centering/alignment balloon 31 may serve as an anchoring device to provide leverage to push an interface member 51 (to be discussed below) against the left atrium (LA) wall (LAW) for optimum contact to assure success. As will be discussed in greater detail below, the centering/alignment balloon 31 serves to center and/or align the guide wire 25 in the pulmonary vein (PV) and/or pulmonary vein ostium (PVO) so that the interface member 51 is coaxially aligned with the pulmonary vein ostium (PVO) to provide optimal coaxial alignment with the pulmonary vein ostium (PVO). The centering/alignment balloon 31 may be designed to have a compliance greater than the compliance of the pulmonary vein (PV) and/or pulmonary vein ostium (PVO) so as to prevent rupture of the pulmonary vein (V) and/or pulmonary vein ostium (PVO) from the forces exerted by an inflated balloon.

Further, in some approaches the interface member 51 (or portions thereof) may be designed to have a compliance greater than the compliance of the pulmonary vein (PV) and/or pulmonary vein ostium (PVO) so as to prevent rupture of the pulmonary vein (PV) and/or pulmonary vein ostium (PVO) from the forces exerted by the interface member's inflated balloon or compartment. The interface member 51 (or portions thereof) having such a compliance serves to center and/or align the guide wire 25, interface member 51 and/or actuator element 61 (e.g., ring or circuit) in the pulmonary vein (PV) and/or pulmonary vein ostium (PVO) so that the interface member 51 and/or actuator element 61 (e.g., ring or circuit) is coaxially aligned (or optimally aligned as desired or required) with the pulmonary vein ostium (PVO) to provide optimal coaxial alignment (or desired/required alignment, e.g., for particular procedures or vasculature characteristics) with the pulmonary vein ostium (PVO).

Additionally, an aspect of the anchoring mechanism achieved by the centering/alignment balloon 31 (or inflatable compartment) is that it may be enabled by a large surface area and hydrostatic forces as opposed to pressure. Thus, this would further minimize the risk of the pulmonary vein (PV) rupture. In one approach, the centering/alignment balloon 31 (or inflatable compartment) may be comprised of a material that will be non-covalently chemically attractive to the endothelia surface. For instance, the material may provide for hydrophilic interaction, hydrostatic forces, hydrophobic interaction and/or molecular flash atomic polaric forces. It should be appreciated that the centering/alignment balloon 31 (or inflatable compartment) may be contoured in any desired/required shape in the longitudinal (x-plane) or radial direction (y and z planes) or combination thereof to provide the entire geometric spectrum of potential shapes in the x, y and z planes.

Further, although not illustrated, in an embodiment the centering/alignment balloon 31 (or inflatable compartment) may further comprise of a rib-like, ring-like, doughnut-like, or rim-like structure or non-compliant portion (referred to as NC) that will be disposed on the proximal end/portion of the balloon when inflated. The rib-like, ring-like, doughnut-like, or rim-like structure will serve to improve the centering and/or aligning of the guide wire 25 in the pulmonary vein (PV) and/or pulmonary vein ostium (PVO) so that the interface member 51 is coaxially aligned with the pulmonary vein ostium (PVO) to provide optimal coaxial alignment with the pulmonary vein ostium (PVO). In addition thereto, the remaining, or distal portion, of the centering/alignment balloon 31 (or inflatable compartment) will maintain large surface area, as discussed above, and shall have a compliance greater than the compliance of the pulmonary vein (PV) and/or pulmonary vein ostium (PVO) so as to prevent rupture of the pulmonary vein (PV) and/or pulmonary vein ostium (PVO) from the forces exerted by the inflated balloon.

Further, the rib-like, ring-like, doughnut-like, or rim-like structure or non-compliant portion (referred to as NC), hereinafter referred to as the "coaxial alignment element," may be sized to a radius of the of the pulmonary vein ostium (PVO) minus a clearance distance as required or desired. The coaxial alignment element of the centering/alignment balloon 31 may be comprised of a variety of sizes according to anatomical and procedural requirements. It should be appreciated that the coaxial alignment element and the centering/alignment balloon may integral with one another, removably coupled together or fixed together. The width of the coaxial alignment element may typically be about 1 mm to about 2 mm, but other desired or required widths may be implemented as well. Additionally, in an approach the coaxial alignment element is not necessarily part of the inflation material but exists there on or adjacent to the inflation material of the balloon and thereby is not part of the inflation function of the remainder of the balloon. Although, in another approach the coaxial alignment element may be inflated, such inflation would be functionally different than the balloon. The coaxial alignment element may be folded/crimped to fit through a catheter or may be inflated/deflated (this inflation again is independent or different from the balloon inflation).

It should be appreciated that the coaxial alignment element may be comprised of a wide variety of geometrical shapes/pattern as well as disposed on various locations of the centering/alignment balloon 31, i.e., not necessarily on the proximal end/portion, and may be on other locations of centering/alignment balloon 31 in addition to the proximal end/portion. For instance, the coaxial alignment element may be spiral shaped (as discussed below regarding FIG. 14) and disposed in communication with at least a portion of the centering/alignment balloon 31. Other geometrical shapes/patterns of the coaxial alignment element may include spiral, x-shaped, zigzag, grid-like, or any geometrical shape/pattern suitable to provide/improve its intended function.

Figure 14:
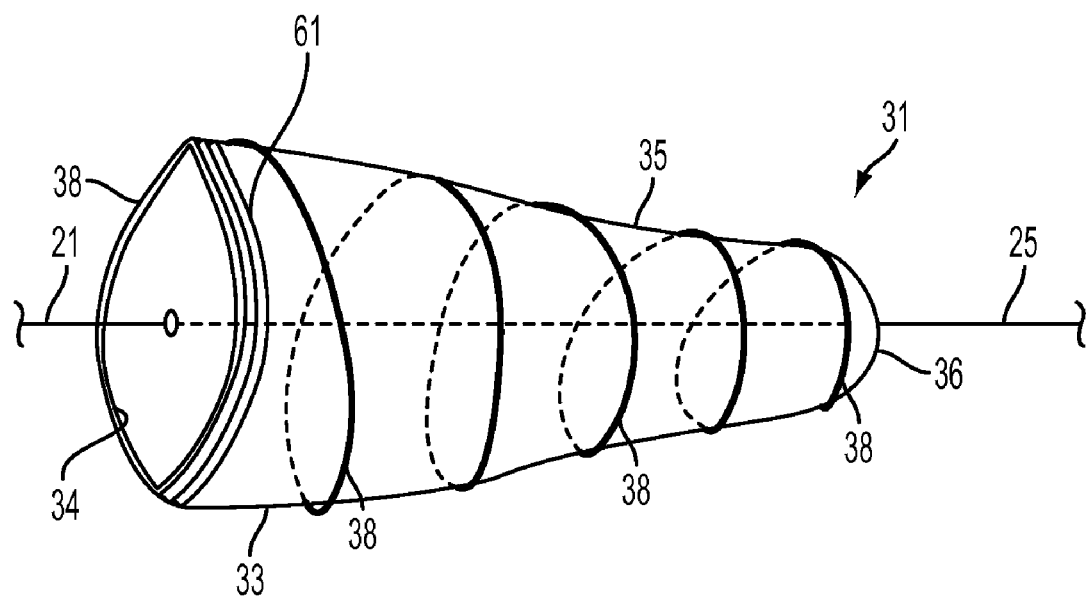
FIG. 14 illustrates a perspective view of an embodiment of the present centering/alignment balloon as shown in the inflated (opened/expanded) state.

Referring to FIG. 14, FIG. 14 in an exemplary embodiment the coaxial alignment element 38 may be spiral shaped and disposed in communication with at least a portion of the centering/alignment balloon 31.

Finally, it should be appreciated that any one of or all of the components discussed herein may be comprised of a non-smooth surface (i.e., varying degrees of smoothness or roughness) that increases surface friction so as to reduce slippage of any of the components discussed herein. One of the components may include the coaxial alignment element, as well as other components, such as balloons, interface members, catheters, and guide wires. In an embodiment, pedicles or the like may be disposed on the component surfaces to improve frictional properties. The pedicles may be applied with various concentrations.

In an embodiment, a ratcheting mechanism may be provided to prevent the interface member 51 from sliding or moving prematurely in a proximal direction, i.e. towards the operator device 17. The ratcheting of the interface member 51 may be accomplished by ratcheting the interface member with the guide wire or catheter, or other components of the ablation assembly 10.

The distal extension 27 may be any desired or required dimension such as about 10 cm or more, about 5 cm or more, 1 cm or more, less than about 1 cm, or less than 1 mm. The distance of the distal extension 27 may be any variable length according to the desired or required procedure/treatment on the subject or patient. At least a portion of the distal extension 27 shall be at or proximal to the PV and/or PVO. In an embodiment, the distal extension 27 may be as short as possible thereby defining the location of the centering balloon 31 at or proximal to the distal tip 29. In addition, a non-traumatic tip balloon 41 (or inflatable compartment) may be disposed at or proximal to the distal wire tip 29. The tip balloon 41 may be the only balloon on the guide wire 21 or the tip balloon 41 may be in addition to the centering/alignment balloon 31. For instances wherein the tip balloon 41 is the only balloon on the guide wire, then the tip balloon 41 may behave as an centering or aligning device in and of itself, such that it serves to center and/or align the guide wire 25 in the PV and/or PVO.

Figure 8:
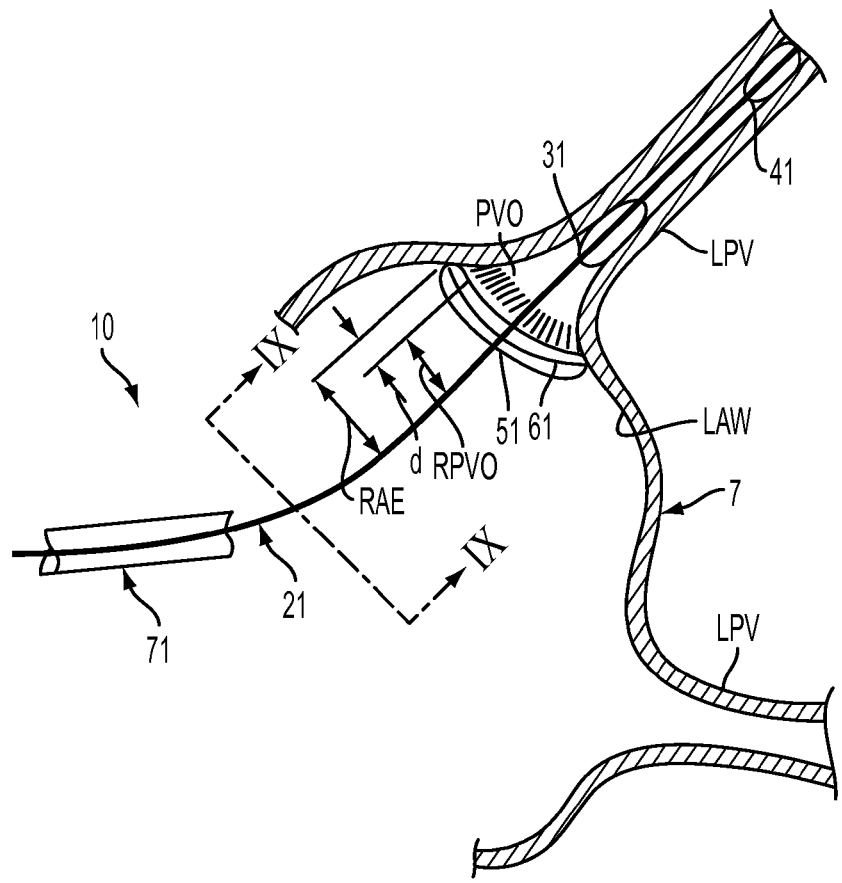
FIGS. 8 and 9 provide exemplary illustrations of dimensions associated with the ablation assembly components relative to the vasculature.
Figure 9:
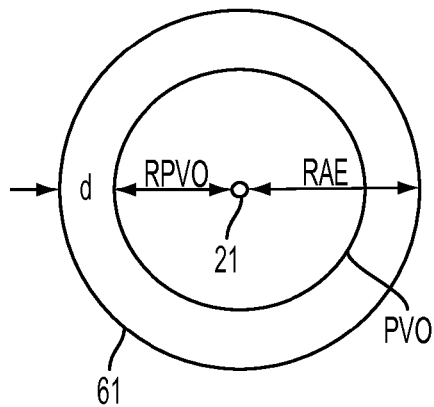

Next, the ablation assembly 10 further includes an interface member 51 that may be positioned at, adjacent or proximal to the PVO (not shown) and which has an actuator element 61 (e.g. ring or circuit) disposed thereon to deliver an energy source, for example radio frequency (RF), ultrasound, or any suitable wavelength of electromagnetic radiation, to the intended contacted tissue of the PVO or desired region. This will now allow the actuator element 61 to create an ablated region or portion 65 that circumscribes the PV and/or PVO as desired or required. For instance, the distance, designated as 'd,' that the ablation region or line 65 is from the PVO may be defined as the difference between radius of the actuator element 61, designated as 'RAE,' and the radius of the PVO, designated as 'RPVO,' whereby the formula is designated as follows: d=RAE−RPVO. See FIGS. 8 and 9 for exemplary illustrations of these dimensions relative to the ablation assembly 10 within a heart 7. FIG. 9 provides a cross-section view IX-IX of FIG. 8 taken at the guide wire 21.

It should be appreciated that a J-tip, non-traumatic tip, or other type of non-traumatic tip may be utilized rather than the tip balloon 41.

Turning to FIG. 2, FIG. 2 illustrates a cross-section view II-II as shown in FIG. 1A of the ablation assembly 10. The guide catheter guide 11 has delivery catheter 71 disposed therein, which in turn has the guide wire 21 disposed therein that provides a guide wire lumen 22 disposed therein. The guide wire lumen 22 may be utilized for a variety of functions, for example, delivering inflation material to the centering/alignment balloon 31 and/or tip balloon 41, as well as any other balloon or inflation devices discussed throughout. The guide wire lumen 22 may be utilized for accommodating a communication channel or wire for delivering energy from the ablation actuator 62 (FIG. 1A) to the ablation element 61 (FIGS. 1-5, 8, 10 and 12) of the interface member 51. Further, the balloons may be inflated by the lumen being connected to an inert gas, radiographic contrast, fluid or air delivery system at the operator end of the catheter, for example. It should be appreciated that a multi-lumen arrangement may be implemented as well. It should be appreciated that a multi-lumen may be implemented with 1) multiple tubes (or the like) or 2) with the approach of a single lumen (tube) having multiple inner compartments, channels, chambers, or lumens each constituting a separate lumen of the device, as well as any combination thereof. Each of the individual lumens or channels may have similar or distinct functions respective to one another. It should be appreciated that the guide wire can vary in diameter throughout its length thereby permitting a larger size lumen or multiple lumens in the larger diameter portion of the wire while maintaining a smaller wire tip capable of better maneuverability (i.e., steerability).

It should be appreciated that the balloons 31, 41 discussed herein (as well as any additional balloons referenced herein) may can take on all shapes along the entire continual geometric spectrum of manipulation of x, y and z planes of the guide wire to create a relatively conical, olive, ellipsoid, hemispherical, tubular, ring, cylindrical, multifaceted or spherical shape with changing of the long and short axes as well as the angle of curvature of the proximal and distal flared surfaces. Size of the balloon or balloon tip could also be manipulated by varying the compliance of the balloon material and inflation pressure. Also, the compliance of the balloon or portions thereof may be provided wherein the balloon compliance is greater than the compliance of pulmonary vein (PV) and/or pulmonary vein ostium (PVO) so as to not rupture of the pulmonary vein (PV) and/or pulmonary vein ostium (PVO) due to the forces imposed by an inflated balloon.

Referring to FIG. 1(B), FIG. 1(B) is similar to the ablation assembly 10 as shown in FIG. 1(A) with the exception, for example, the ablation assembly operates with one less catheter. In the particular arrangement illustrated in FIG. 1(B) the delivery catheter is omitted as compared to the arrangement shown in FIG. 1(A).

Figure 3:
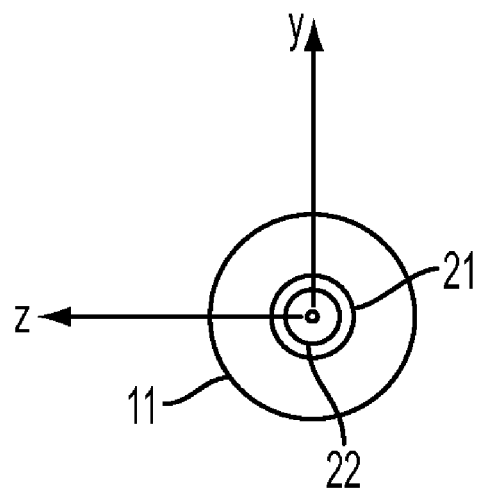
FIG. 3 illustrates a cross-section view III-III as shown in FIG. 1(B) of the ablation assembly.

Turning to FIG. 3, FIG. 3 illustrates a cross-section view III-III as shown in FIG. 1(B) of the ablation assembly 10, whereby the guide catheter guide 11 has the guide wire 21 disposed therein without the delivery catheter 71 disposed therein, as provided in the assembly of FIG. 2.

It should be appreciated that any the interface members discussed herein may take on all shapes along the entire continual geometric spectrum of manipulation of x, y and z planes of the guide wire and PV and/or PVO to create a relatively conical, olive, ellipsoid, hemispherical, tubular, ring, cylindrical, multifaceted or spherical shape with changing of the long and short axes as well as the angle of curvature of the proximal and distal flared surfaces. Size of the interface member could also be manipulated by varying the compliance or structural integrity of the interface member or portions thereof. For instance, any of the attributes, functions, and features discussed herein associated with the centering/alignment balloon may be applied to the interface members discussed herein. For instance, in some approaches the interface member 51 (or portions thereof) may be designed to have a compliance greater than the compliance of the pulmonary vein (PV) and/or pulmonary vein ostium (PVO) so as to prevent rupture of the pulmonary vein (PV) and/or pulmonary vein ostium (PVO) from the forces exerted by its inflated balloon or compartment. The interface member 51 (or portions thereof) having such a compliance serves to center and/or align the guide wire 25, interface member 51 and/or actuator element 61 (e.g., ring or circuit) in the pulmonary vein (PV) and/or pulmonary vein ostium (PVO) so that the interface member 51 and/or actuator element 61 (e.g., ring or circuit) is coaxially aligned (or optimally aligned) with the pulmonary vein ostium (PVO) to provide optimal coaxial alignment (or alignment as desired or required, e.g., for particular procedures or vasculature characteristics) with the pulmonary vein ostium (PVO).

The interface member 51 may include a distal end, distal portion, proximal end and proximal portion, having a desired/required radius that may vary along its continuum. At least a portion of the proximal portion may include a coaxial alignment element such as a non-compliant portion, referenced as NC, which may comprise a non-compliant material or structure in whole or in part. The NC of the balloon (compartment or structure) can be a variety of lengths extending from or proximity thereto the proximal end of the balloon (compartment or structure) as desired/required being "x" distance distal from the proximal end (or proximally thereto) of the balloon (compartment or structure). Moreover, any portion of the NC of the balloon (compartment or structure) can have wide variety of potential shapes. For instance, it should be appreciated that the NC of the centering/alignment balloon (structure or compartment) may be contoured in any desired/required shape in the longitudinal direction (x-plane) or radial direction (y and z planes) or combination thereof to provide the entire geometric spectrum of potential shapes in the x, y and z planes. For example, the shape may be bell-shaped, olive shaped, hemispherical shaped, ellipsoid shaped or multifaceted shaped, cone shaped, oval shaped, etc.

As discussed above, NC of the interface member serves to center and/or align the guide wire, interface member, and/or actuator element in the pulmonary vein (PV) and/or pulmonary vein ostium (PVO) so that the interface member and/or actuator element is coaxially aligned or optimally aligned with the pulmonary vein ostium (PVO) to provide optimal coaxial alignment (or desired/required alignment as necessary, e.g., for particular procedures or vasculature characteristics/abnormalities/irregularities) with the pulmonary vein ostium (PVO). The remaining portion of the interface member that is not the NC may be designed to have a compliance greater than the compliance of the pulmonary vein (PV) and/or pulmonary vein ostium (PVO) so as to prevent rupture of the pulmonary vein (PV) and/or pulmonary vein ostium (PVO) from the forces exerted by an inflated balloon (or compartment or structure).

It should be further appreciated that in some approaches the centering/alignment balloon may be provided with an actuator element thereon the centering/alignment balloon and the general methodology and design as discussed throughout can be practiced or implemented 1) without an interface member or 2) with an interface member but without the interface member providing the actuator element function.

Figure 4A:
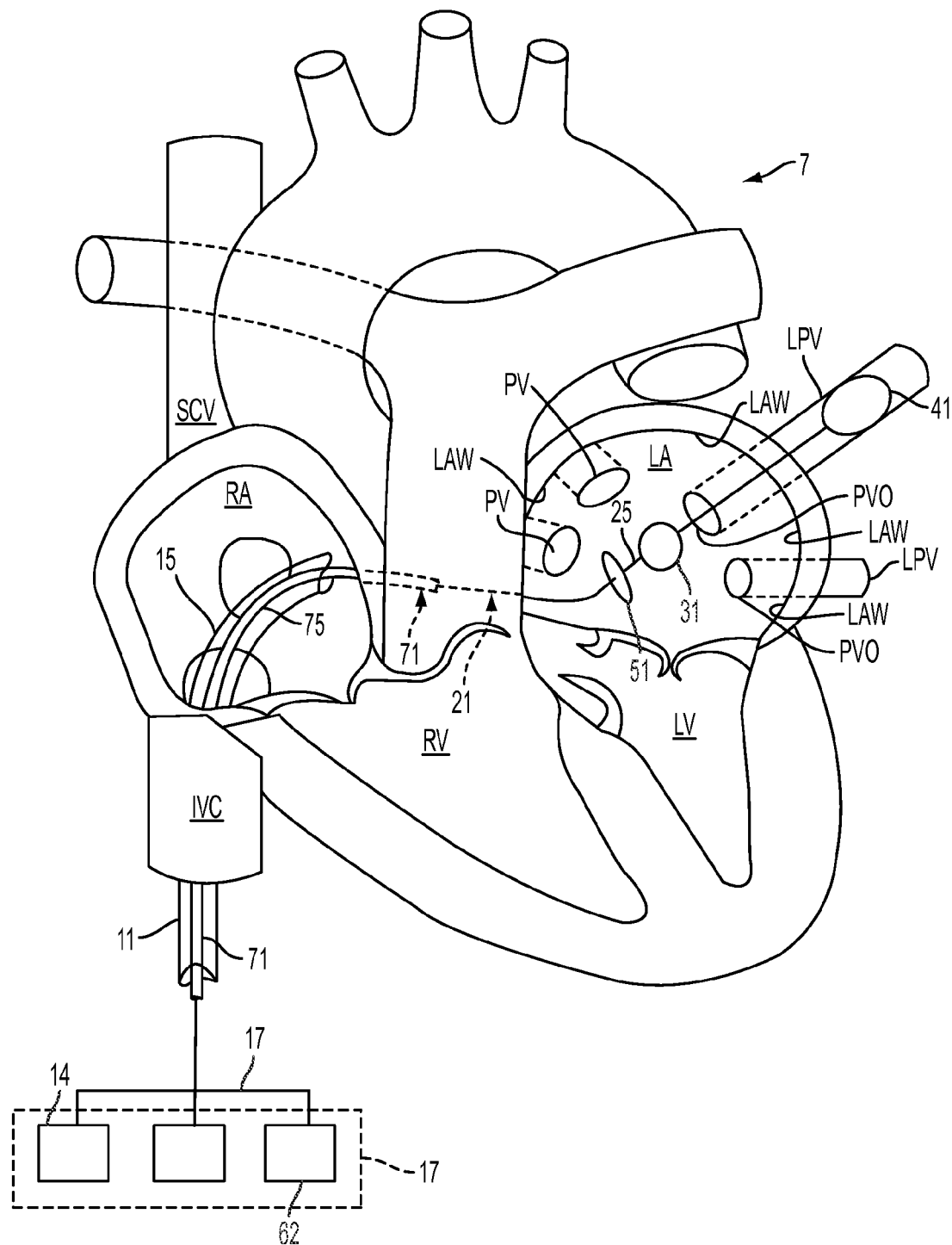
FIG. 4(A) and FIG. 5(A) schematically illustrate use of the catheter device of FIG. 1(A) within a heart.
Figure 5A:
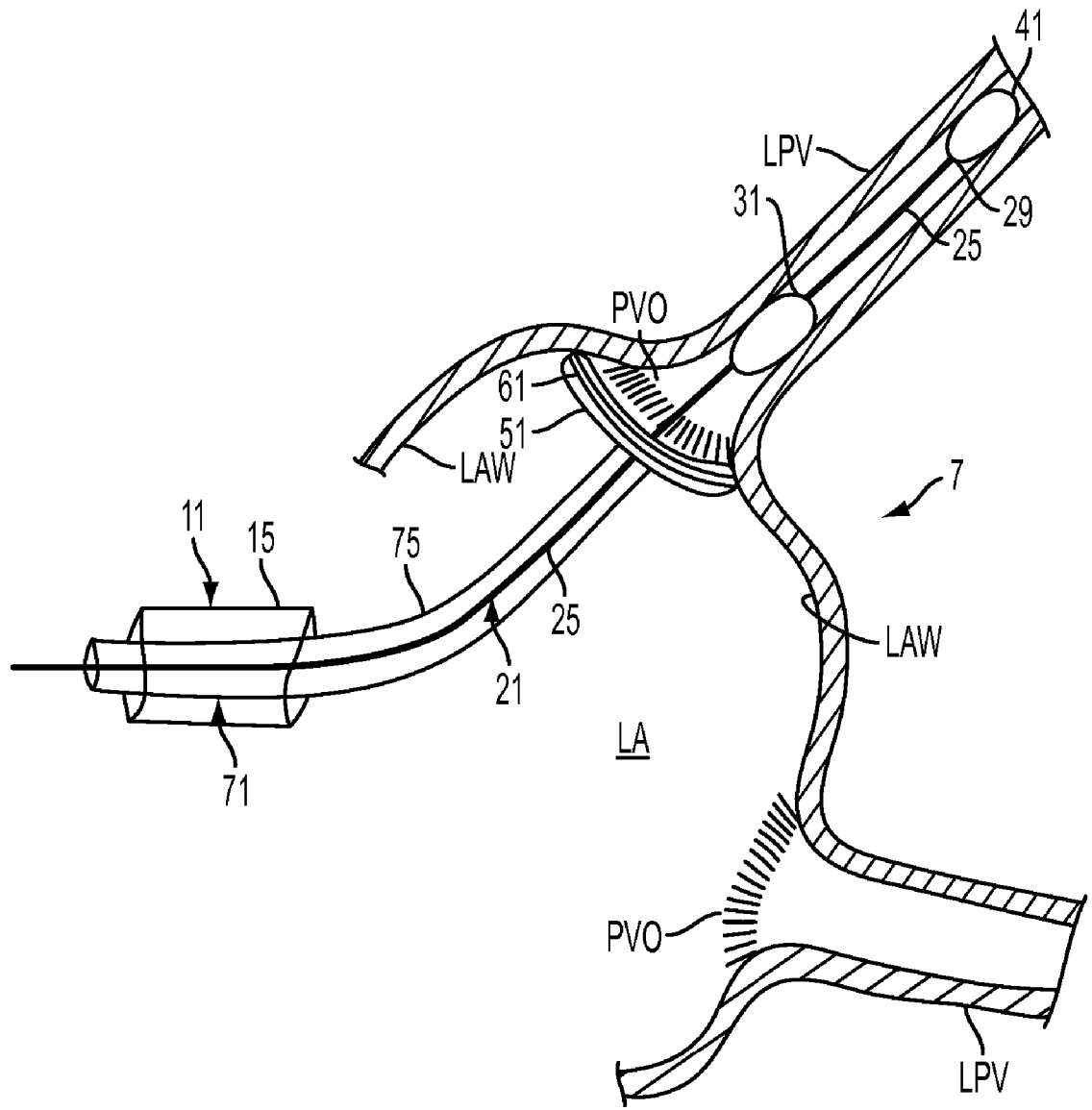

FIGS. 4(A) and 5(A) illustrate use of the ablation assembly 10 shown in FIG. 1A within a heart 7. As a point of reference, the heart 7 includes a right atrium (RA), a left atrium (LA), a right ventricle (RV) and a left ventricle UV). An inferior vena cava (IVC) and a superior vena cava (SVC) lead into the right atrium RA. The right atrium RA is separated from the left atrium LA by an interarterial septum (not shown). Finally, four pulmonary veins (PV) extend from the left atrium LA. Each of the pulmonary veins PV forms an ostium (PVO) in the left atrium (LA) wall (LAW). As an example, during formation of the heart 7, it is possible that tissue of the left atrium LA may grow upwardly into one or more of the pulmonary veins PV. This left atrium LA tissue may spontaneously depolarize, resulting in atrial fibrillation. Notably, the heart 7 may be formed such that a separate ostium PVO is not formed for each individual pulmonary vein PV. In other words, a single pulmonary vein ostium PVO may be formed for two pulmonary veins PV. For example, a single pulmonary vein ostium PVO may be formed for both the left inferior pulmonary vein PV and the left superior pulmonary vein PV, with the two pulmonary veins PV bifurcating from the single ostium PVO.

As shown in FIG. 4(A), interaction with the pulmonary vein PV begins by directing the distal portion 25 of the guide wire 21 through the inferior vena cava IVC, into the right atrium (RA) through a puncture in the interarterial septum (not shown) and into the left atrium (LA). Alternatively, the introduction of the distal portion 15 of the guide catheter shaft 12 and delivery catheter 71 into the right atrium (RA) is also suggested by passage of the distal portion 15 into the right atrium (RA) through the superior vena cava (SVC). The tip balloon 41 is positioned inside the LPV and the interface member 51 and centering/alignment balloon 31 is shown in the LA prior to being positioned at or into the PV and/or PVO.

Figure 5B:
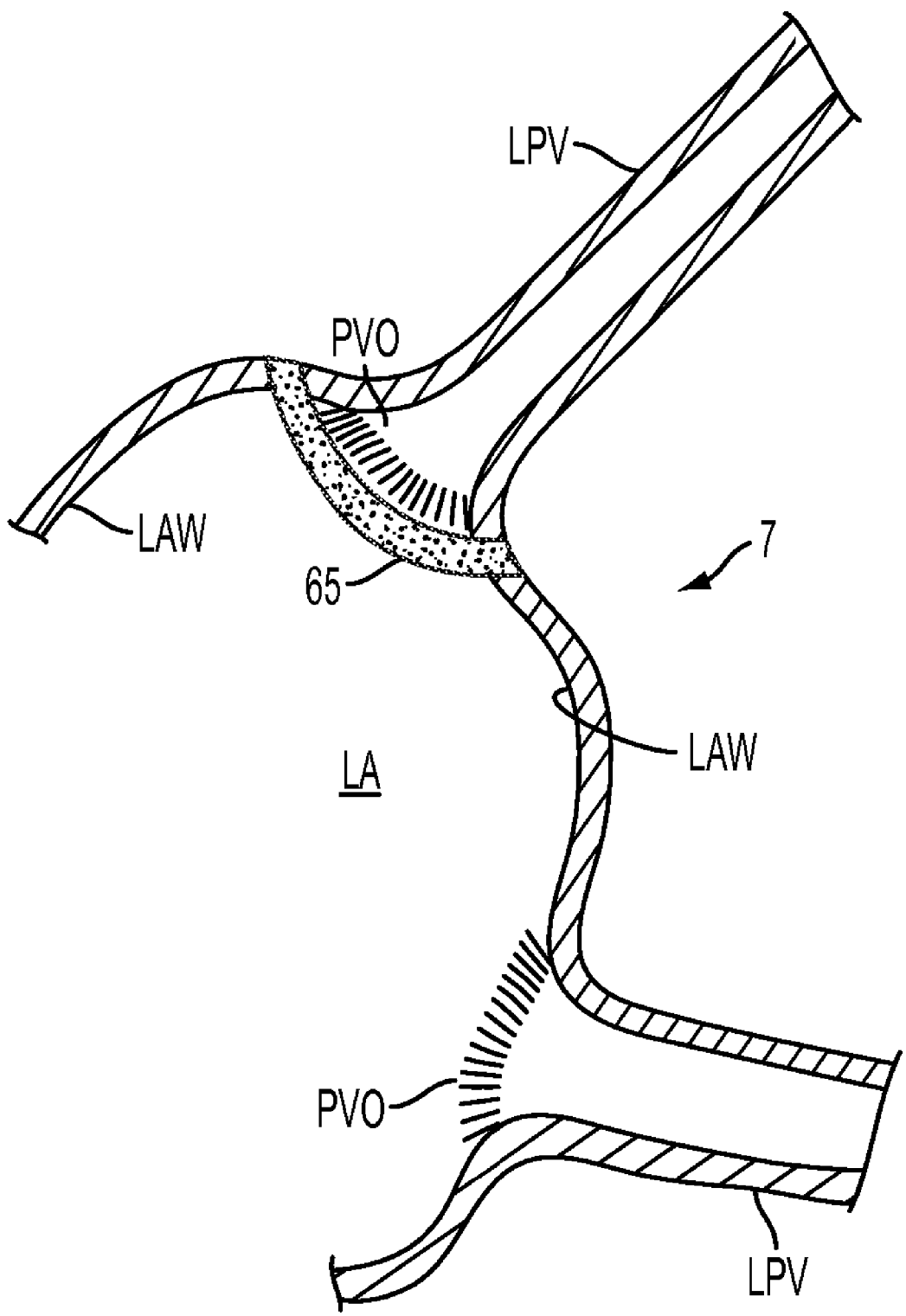
FIG. 5(B) schematically illustrates the resultant symmetric ablation line/region 65 created by the assembly shown in FIG. 5(A).

As shown in FIG. 5(A), the tip balloon 41 is disposed inside the LPV and the interface member 51 and centering/alignment balloon 31 are advanced at or proximal to at the PV and/or PVO so as to be in a position that enables the actuator element 61 (e.g., ring or circuit) to create a coaxial alignment with the pulmonary vein (PV) and/or pulmonary vein ostium (PVO) thus enabling a symmetric ablation line/region 65 (see FIG. 5(B)) with the pulmonary vein (PV) and/or pulmonary vein ostium (PVO), i.e., the distance from the ablation line to the pulmonary vein ostium (PVO) does not vary. Accordingly, an ablated region or portion 65 (see FIG. 5(B)) is created that circumscribes the PV and/or PVO as desired or required.

The ablation element 61 is energized via the ablation actuator 62 (FIG. 1A) to a sufficient level to ablate the contacted tissue as desired or required, using for example, cryogenic therapy, a radio frequency (RF) source, ultrasound source, or any suitable wavelength of electromagnetic radiation. As a result, a continuous, closed lesion pattern 65 is formed around or adjacent to the PVO as shown in FIG. 5(b)). Pursuant to the configuration, a continuous, closed ablation pattern is achieved at or adjacent to the PVO.

It should be appreciated that the centering/alignment balloon 31 may be a wide range of distances from the distal tip 29, whereby the distal extension 27 can be designed according to required or desired procedure/treatment and anatomy of the vasculature.

In an embodiment, a tip balloon 41 may be disposed at or proximal to the distal wire tip 29, whereby the tip balloon 41 (designed to prevent vessel trauma) may be the only balloon on the guide wire 21 or the tip balloon 41 may be in addition to the centering/alignment balloon 31. For instances whereby the tip balloon 41 is the only balloon on the guide wire, then the tip balloon 41 may behave as an cente ring/alignment device in and of itself, such that it serves as a positioning the guide wire 21 and/or interface member 51.

It should be appreciated that any of the centering/alignment balloons 31 referenced herein (or portions of the balloons) may have any of the attributes, sizes, elements and functions as discussed throughout this document. For example, but not limited thereto, any of the coaxial alignment elements (or functions) such as the NC or rib-like, ring-like, doughnut-like, or rim-like structure may be integrally or separately formed with, disposed on, or in communication with the centering/alignment balloon 31.

Figure 4B:
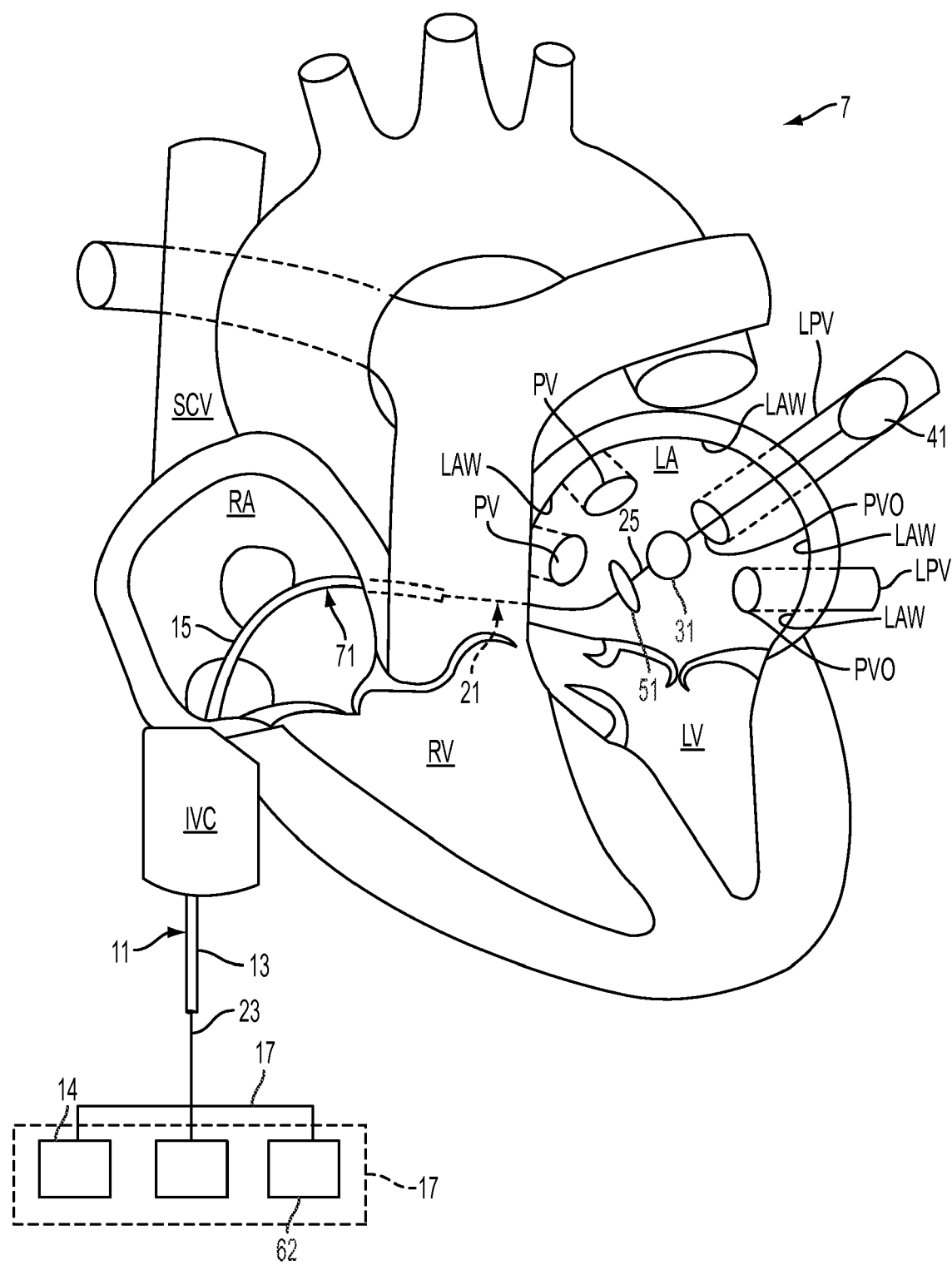
FIG. 4(B) schematically illustrates use of the catheter device of FIG. 1(B) within a heart.

Similarly, FIG. 4(B) also illustrates the use of the ablation assembly 10 shown in FIG. 1(B) within a heart 7.

Figure 6A:
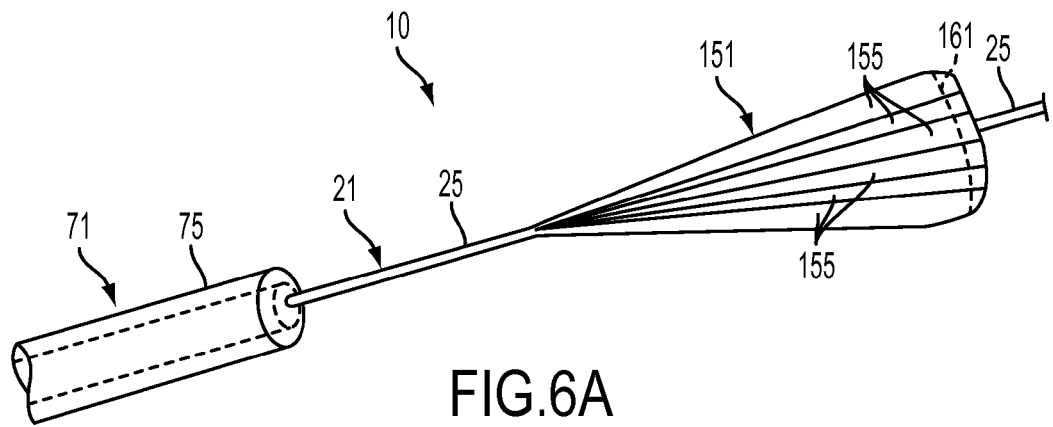
FIGS. 6(A)-(B) illustrate a perspective view of an embodiment of the present invention ablation assembly as shown in the deflated (restricted) state and the inflated (expanded) state, respectively.

Turning to FIG. 6(A), FIG. 6(A) illustrates a perspective partial view of an embodiment of the present invention ablation assembly 10 including a delivery catheter 71 having a distal portion 75 of the catheter guide, a guide wire 21, and an interface member 151 that may be positioned at, adjacent or proximal to the PVO (not shown) and which has an actuator element 161 (e.g. ring or circuit) disposed thereon to deliver an energy source, for example cryogenic therapy, radio frequency (RF) (or other energy sources such as ultrasound source, or any suitable wavelength of electromagnetic radiation), to the intended contacted tissue of the PVO or desired region. This will now allow the actuator element 161 to create an ablated region or portion that circumscribes the PV and/or PVO as desired or required. The interface member 151 is a balloon (or inflatable or expandable compartment) having a plurality of panels 155. The plurality of panels 155 may be individual segments or one continuous surface. The interface member 151 is shown in the deflated (restricted) state and the inflated (expanded) state in FIG. 6(A) and FIG. 6(B), respectively. The panels 155 may be folded over top of each other in the deflated state, or any other available arrangement to achieve size reduction.

Figure 6B:
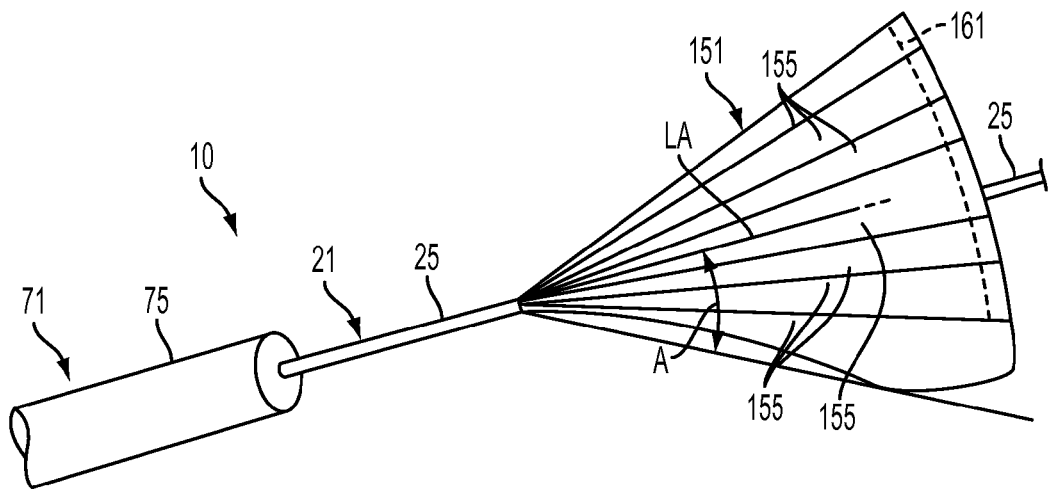

Still referring to FIG. 6(B), for illustration purposes only, a longitudinal axis (referenced as LA) is depicted to define the general angle (referenced as A) that the interface member 151 flares or angles outward. It should be appreciated that the interface member 151 may be contoured or structured to be a variety of shapes and sizes to accommodate successful ablation. For example, the shape may be bell-shaped, olive shaped, hemispherical shaped, ellipsoid shaped or multifaceted shaped, cone shaped, oval shaped, etc. The angle, A, may comprise a number of settings or ranges, for example, between about 0 degrees and about 180 degrees (or any angle there between), between about 30 degrees and about 150 degrees, between about 45 degrees and about 135 degrees, about 60 degrees, about 45 degrees, about 30 degrees, or any desired or required limit. The sides or walls of the interface member 151 may be shaped along the entire geometric spectrum of potential shapes in the x, y and z planes.

It should be appreciated that if the angle, A, is smaller then a decrease in the amount of folding of the panels may be achieved. Conversely, if the angle, A, is larger then an increase in the amount of folding of the panels may be required. Also, the circuit, transmission path or contact that transmits energy from the ablation actuator 62 (See FIG. 1) to the actuator element 161 may be run in a variety of paths. For example, one approach would be to run the circuit, transmission path or contact along the longitudinal access LA and radially across to the rim of the interface member 155 or ablation element 161. Alternatively, the circuit, transmission path or contact may run along the wall of the interface member 155 to reach the rim of the interface member 155 or ablation element 161. The transmission path may be hard wired or wireless.

In an embodiment, the interface member 151 may be comprised of a shape memory alloy (SMA) wherein upon the appropriate stimulus/activation the interface member 151 can change between a deployed (larger) state and reduced (smaller state) in accordance with SMA properties and functions.

In an embodiment, a sheath (not shown) may be inserted into the heart, or other vasculature such as an artery, vein, or the like. The sheath may be utilized wherein the interface member 151 extends or passes there through. The interface member 151 may be compressible whereby during use of the ablation assembly the interface member 151 is passed through the lumen of the sheath 241 in a compressed state and expands after it exits the end or orifice of the sheath.

Figure 6C:
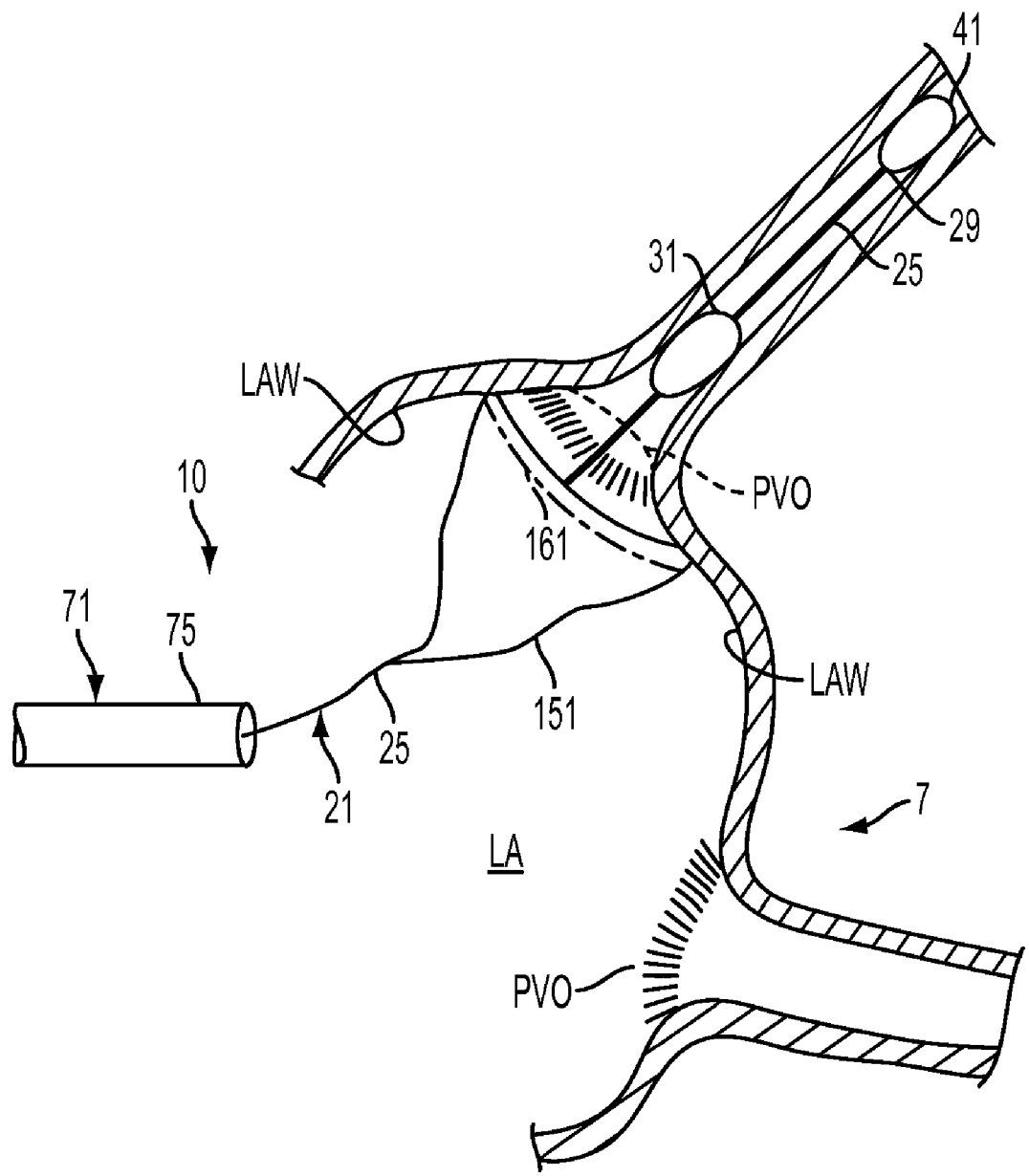
FIG. 6(C) schematically illustrates use of the ablation assembly of FIGS. 6(A)-(B) within a heart.

Next, as shown in FIG. 6(C), the tip balloon 41 is disposed inside the LPV and the interface member 151 and centering/alignment balloon 31 are advanced at or proximal to at the PV and/or PVO so as to be in a position that enables the actuator element 161 (e.g., ring or circuit) to create an ablated region or portion (as similarly shown in FIG. 5(B)) that circumscribes the PV and/or PVO as desired or required. The interface member 151 may be inflated and positioned accordingly against the LAW with optimal coaxial alignment with the centering/alignment balloon 31 to provide leverage to push the interface member 151 against the left atrium wall (LAW). Next the ablation element 161 may be energized via the ablation actuator 62 (FIG. 1(A)) to a sufficient level to ablate the contacted tissue as desired or required, using for example, cryogenic therapy, a radio frequency (RF) source, ultrasound source, or any suitable wavelength of electromagnetic radiation.

Figure 7A:
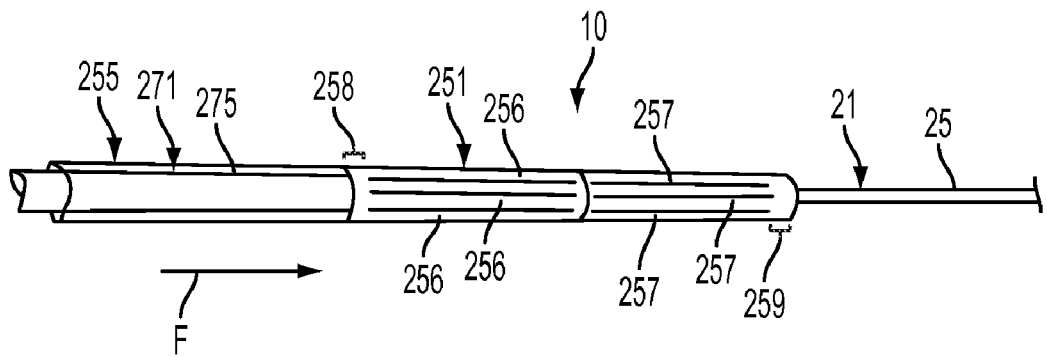
FIGS. 7(A)-(B) illustrate a perspective view of an embodiment of the present invention ablation assembly as shown in the non-deployed (closed) state and the deployed (opened/flared) state, respectively.

Turning to FIG. 7(A), FIG. 7(A) illustrates a perspective partial view of an embodiment of the present invention ablation assembly 10 including a delivery catheter 271 having a distal portion 275 of the delivery catheter 271, a guide wire 21, and an interface member 251 that may be positioned at, adjacent or proximal to the PVO (not shown) and which has an actuator element 261 (not shown, e.g. intended ring or circuit) disposed thereon to deliver an energy source, for example radio frequency (RF) (or ultrasound source, or any suitable wavelength of electromagnetic radiation source), to the intended contacted tissue of the PVO or desired region.

Figure 7B:
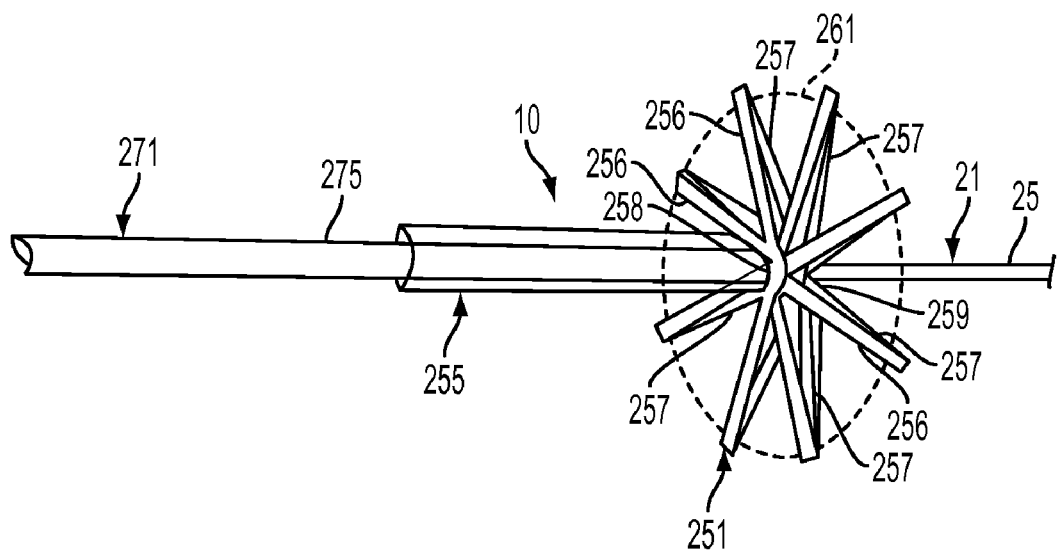

Fixably or removably disposed on the delivery catheter 271 is a is distal hub 259 having a plurality of distal spokes 257 attached thereto, and shown in the non-deployed position. Slidably disposed on the delivery catheter 271 is a proximal hub 258 having a plurality of proximal spokes 256 attached thereto, and shown in the non-deployed position. A sleeve member 255 is slidably disposed over delivery catheter 271 and in communication with the proximal hub 258 and the operator end (not shown) of the ablation assembly 10. An ablation element 261 (not shown) may be folded/collapsed/arranged on the under side of the proximal spokes 256 and/or distal spokes 257. While the spokes are in a collapsed state the ablation element wire may be folded in an accordion-like manner and will not be visible. Next, referring to FIG. 7(B), as a result of a force, as designated as F in FIG. 7(A), that is applied to the proximal hub 258 the proximal hub may be pushed as close to the distal hub 259 as possible, or as desired, thereby causing the proximal and distal set of spokes 256, 257 to be deployed and flare outward allowing the ablation element 261 to unfold or release so as to form a rim or ring. As the proximal and distal spokes emanate from their respective hubs and whereby the hubs are located close one another then a structure not unlike a bicycle wheel may result. In a deployed state, the ablation element 261 may occupy a rim created by the tips of the spokes. It should be appreciated that the hub and spokes can be low enough profile to create as flat a disk as possible (i.e., less angulation than is seen for a bike wheel). While energized the actuator element 261 creates an ablated region or portion that circumscribes the PV and/or PVO as desired or required.

Conversely, when the proximal hub 258 is pulled or slid away from the distal hub 259 the proximal and distal spokes will collapse onto the delivery shaft 212 of the delivery catheter 271 and the actuator element wire 261 will require accordion folding or other folding/arranging/collapsing and may not be visible.

Figure 7C:
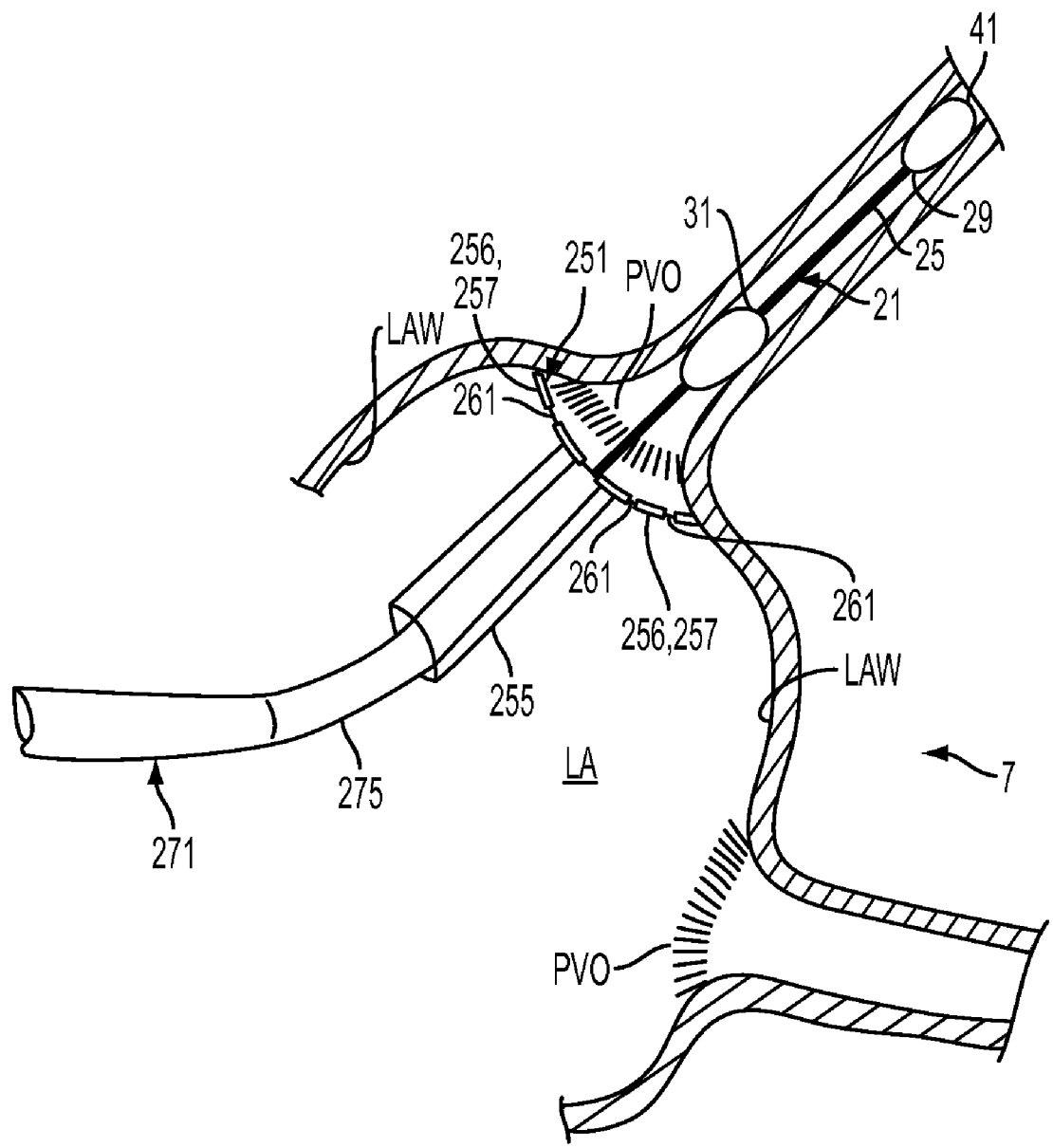
FIG. 7(C) schematically illustrates use of the ablation assembly of FIGS. 7(A)-(B) within a heart.

Next, as shown in FIG. 7(C), the tip balloon 41 is disposed inside the LPV and the interface member 251 and centering/alignment balloon 31 are advanced at or proximal to at the PV and/or PVO so as to be in a position that enables the actuator element 261 (e.g., ring or circuit) to create an ablated region or portion (as similarly shown in FIG. 5(B), for example) that circumscribes the PV and/or PVO as desired or required.

With the interface member 251 deployed and positioned accordingly against the LAW and PVO the ablation element 261 is energized via the ablation actuator 62 (FIG. 1) to a sufficient level to ablate the contacted tissue as desired or required, for example with a cryogenic therapy, radio frequency (RF) source, ultrasound source, or any suitable wavelength of electromagnetic radiation source. It should be appreciated that other available energy source or stimulation may be utilized for any of the embodiments discussed herein.

Figure 10A:
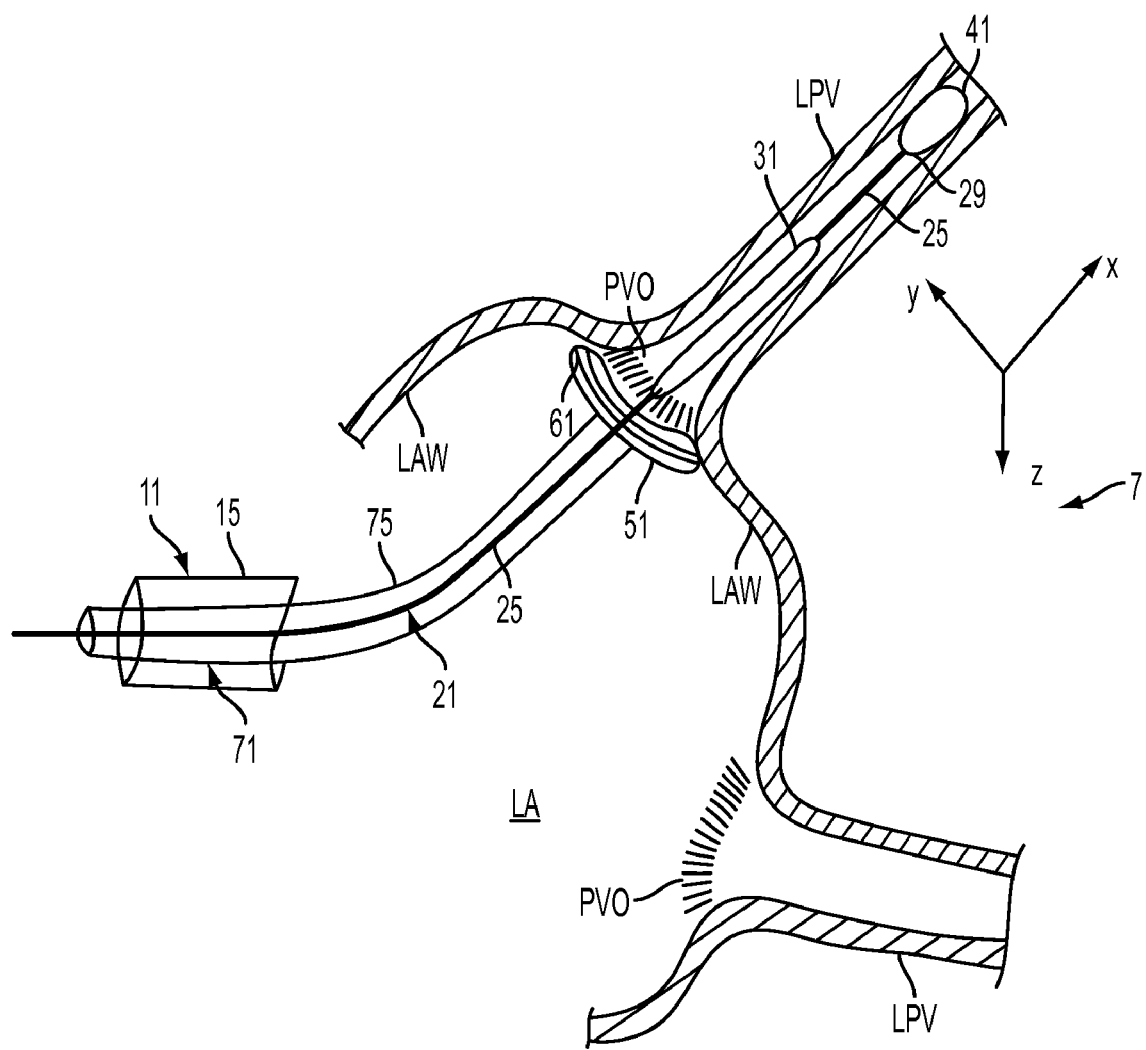
FIG. 10(A) and FIG. 10(B) schematically illustrate the use of an ablation assembly within a heart wherein the centering/alignment balloon is shown in the non-deployed (restricted/closed) state and the deployed (opened/expanded) state, respectively.
Figure 10B:
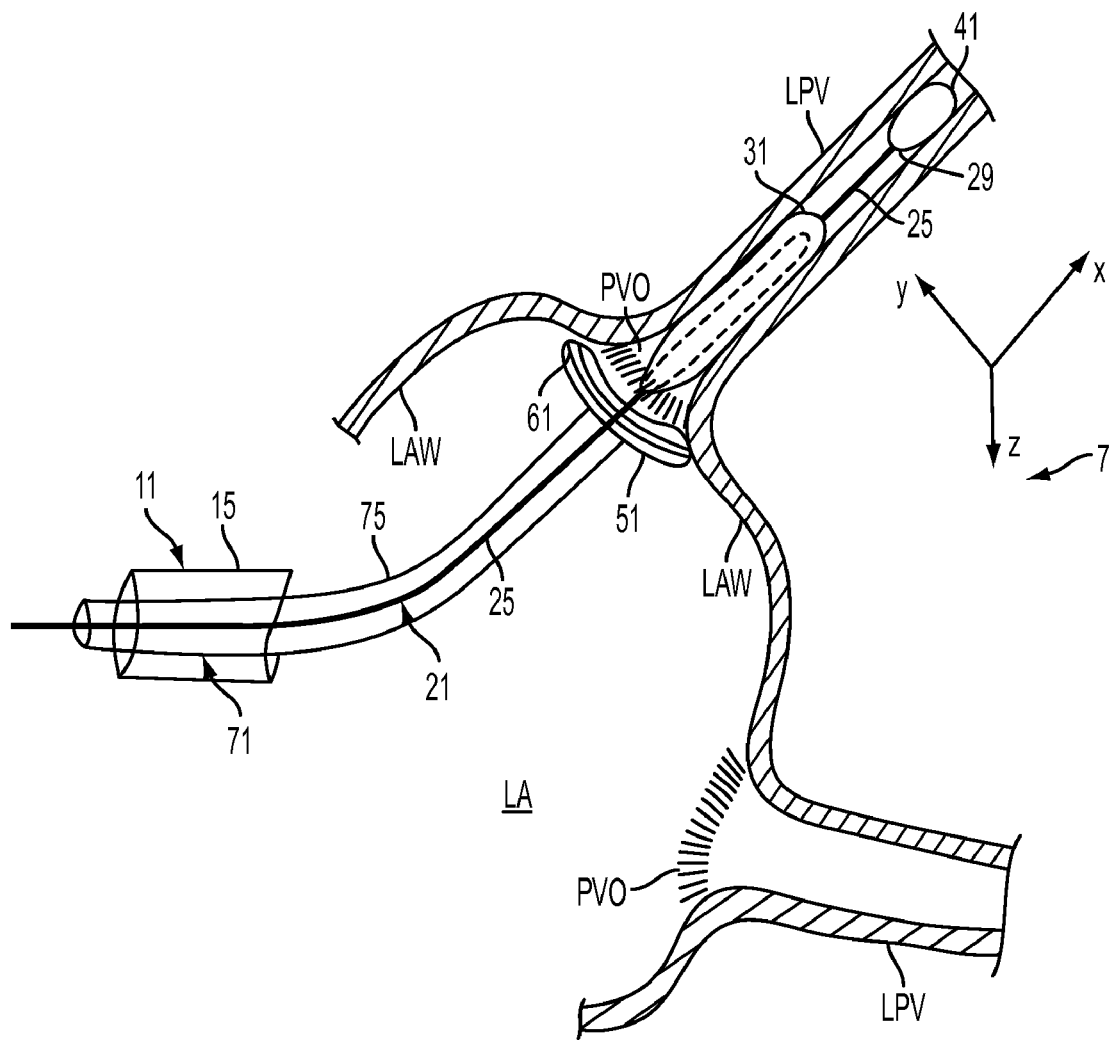

Referring to FIG. 10(A) and FIG. 10(B), FIG. 10(A) and FIG. 10(B) schematically illustrate the use of an ablation assembly within a heart wherein the centering/alignment balloon 31 is shown in the non-deployed (restricted/closed) state and the deployed (opened/expanded) state, respectively. As shown in FIG. 10(A), the tip balloon 41 is disposed inside the LPV and the interface member 51 and centering/alignment balloon 31 (deflated/restricted) may be advanced at or proximal to at the PV and/or PVO. As shown in FIG. 10(B), the centering/alignment balloon 31 may be positioned and inflated/expanded enabling the actuator element 61 (e.g., ring or circuit) to create a coaxial alignment with the pulmonary vein (PV) and/or pulmonary vein ostium (PVO); and thus enabling a symmetric ablation line/region (not shown) with the pulmonary vein (PV) and/or pulmonary vein ostium (PVO), i.e., the distance from the ablation line/region to the pulmonary vein ostium (PVO) does not vary. Accordingly, an ablated region or portion is created that circumscribes the PV and/or PVO as desired or required.

Figure 11A:
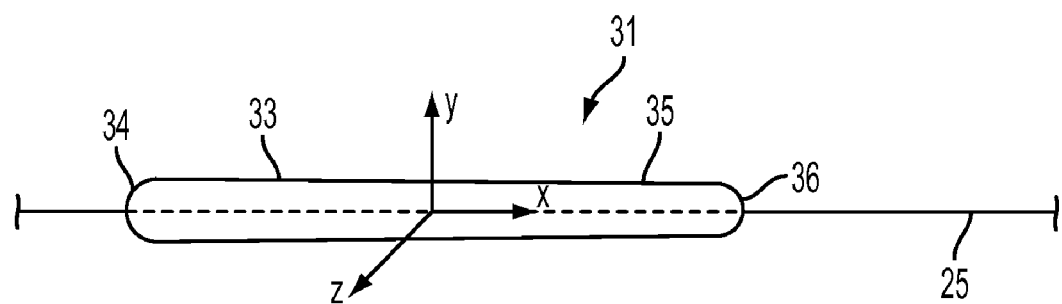
FIGS. 11(A) and 11(B) illustrate a perspective view of an embodiment of the present centering/alignment balloon as shown in the deflated (restricted/closed) state and the inflated (opened/expanded) state, respectively.
Figure 11B:
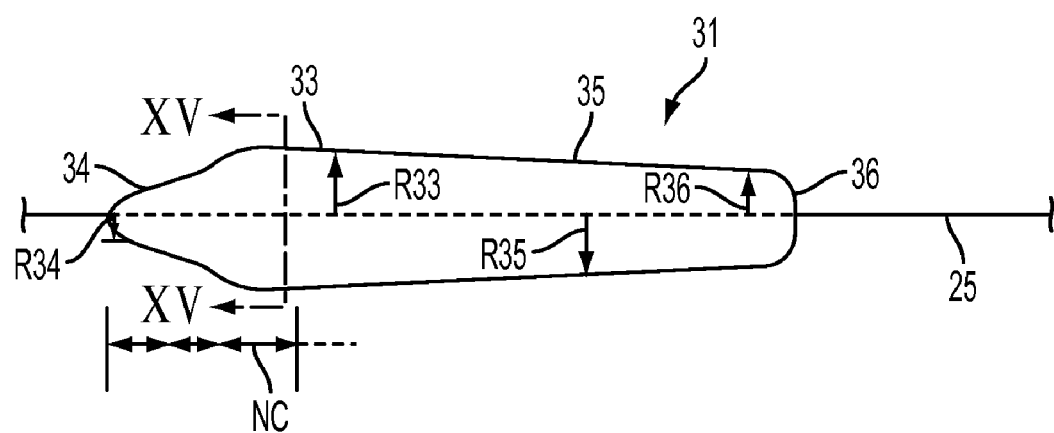

Turning to FIGS. 11(A) and 11(B), FIGS. 11(A) and 11(B) illustrate a perspective view of the present centering/alignment balloon 31 of FIG. 10 in the deflated (restricted/closed) state and inflated (opened/expanded) state, respectively. The centering/alignment balloon 31 includes a distal end 36, distal portion 35, proximal end 34 and proximal portion 33, having a desired/required radius R33 that may vary along its continuum. At least a portion of the proximal portion 33 includes a coaxial alignment element such as a non-compliant portion, referenced as NC, which may comprise a non-compliant material or structure in whole or in part. The NC of the balloon 31 can be a variety of lengths extending from or proximity thereto the proximal end 34 of the balloon 31 as desired/required being "x" distance distal from the proximal end 34 (or proximally thereto) of the balloon 31. Moreover, any portion of the NC of the balloon can have wide variety of potential shapes. For instance, it should be appreciated that the NC of the centering/alignment balloon 31 may be contoured in any desired/required shape in the longitudinal direction (x-plane) or radial direction (y and z planes) or combination thereof to provide the entire geometric spectrum of potential shapes in the x, y and z planes. For example, the shape may be bell-shaped, olive shaped, hemispherical shaped, ellipsoid shaped or multifaceted shaped, cone shaped, oval shaped, etc.

As discussed above, NC of the centering/alignment balloon 31 serves to center and/or align the guide wire 25 in the pulmonary vein (PV) and/or pulmonary vein ostium (PVO) so that the interface member 51 is coaxially aligned with the pulmonary vein ostium (PVO) to provide optimal coaxial alignment with the pulmonary vein ostium (PVO). The remaining portion of the centering/alignment balloon 31 that is not the NC may be designed to have a compliance greater than the compliance of the pulmonary vein (PV) and/or pulmonary vein ostium (PVO) so as to prevent rupture of the pulmonary vein (PV) and/or pulmonary vein ostium (PVO) from the forces exerted by an inflated balloon 31 (or compartment).

Further, the high compliance of the remaining portions/wills (i.e., portions other than the NC) of the centering/alignment balloon 31 provides additional aspects/functions. For instance the high compliance walls of the balloon provide an anchoring mechanism enabled by a large surface area and hydrostatic forces as opposed to pressure. In one approach, the high compliance walls of the centering/alignment balloon 31 (or inflatable compartment) may be comprised of a material that will be non-covalently chemically attractive to the endothelia surface. For instance, the material may provide for hydrophilic interaction, hydrostatic forces, hydrophobic interaction and/or molecular flash atomic polaric forces.

Figure 15:
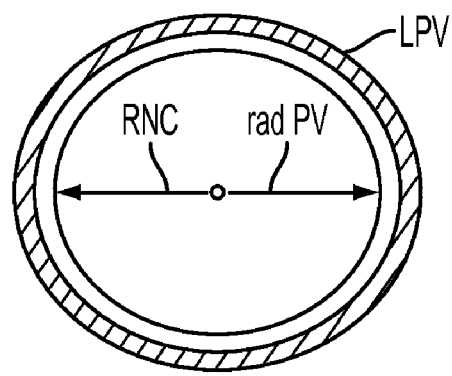
FIG. 15 provides a cross-section view XV-XV of FIG. 11(B) that provides an exemplary illustration of dimensions associated with the centering/alignment balloon 31 in relation to the pulmonary vein.

Turning to FIG. 15, FIG. 15 provides a cross-section view XV-XV of FIG. 11(B) that provides an exemplary illustration of dimensions associated with the centering/alignment balloon 31 in relation to the pulmonary vein. As shown in FIG. 15, the maximal diameter of the radius of the NC (designated as 'RNC') of the centering/alignment balloon 31 is equal to the diameter of the radius of the PV (designated as 'radPV') minus y or z (in the radial direction).

Figure 12A:
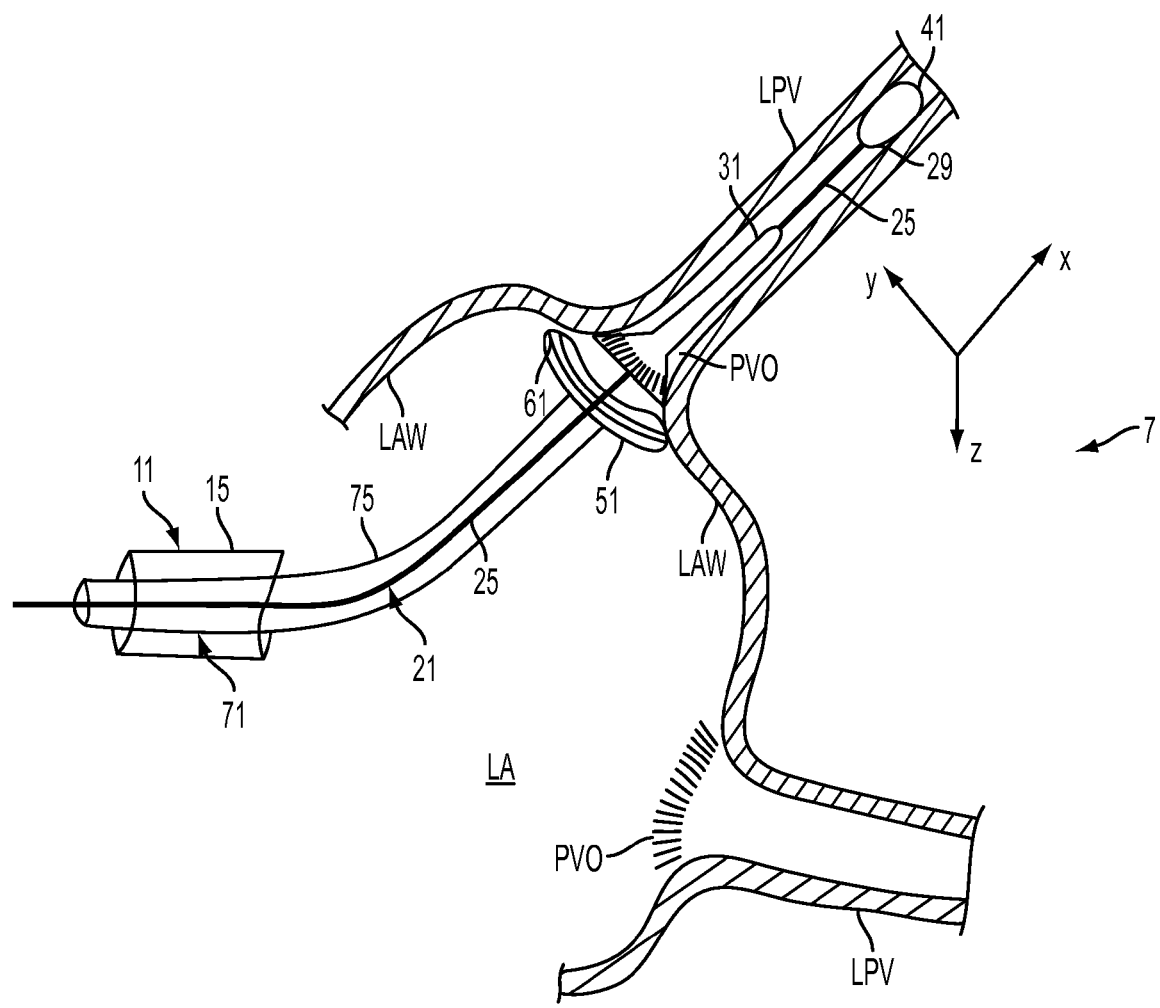
FIG. 12(A) and FIG. 12(B) schematically illustrate the use of an ablation assembly within a heart wherein the centering/alignment balloon is shown in the non-deployed (restricted/closed) state and the deployed (opened/expanded) state, respectively.
Figure 12B:
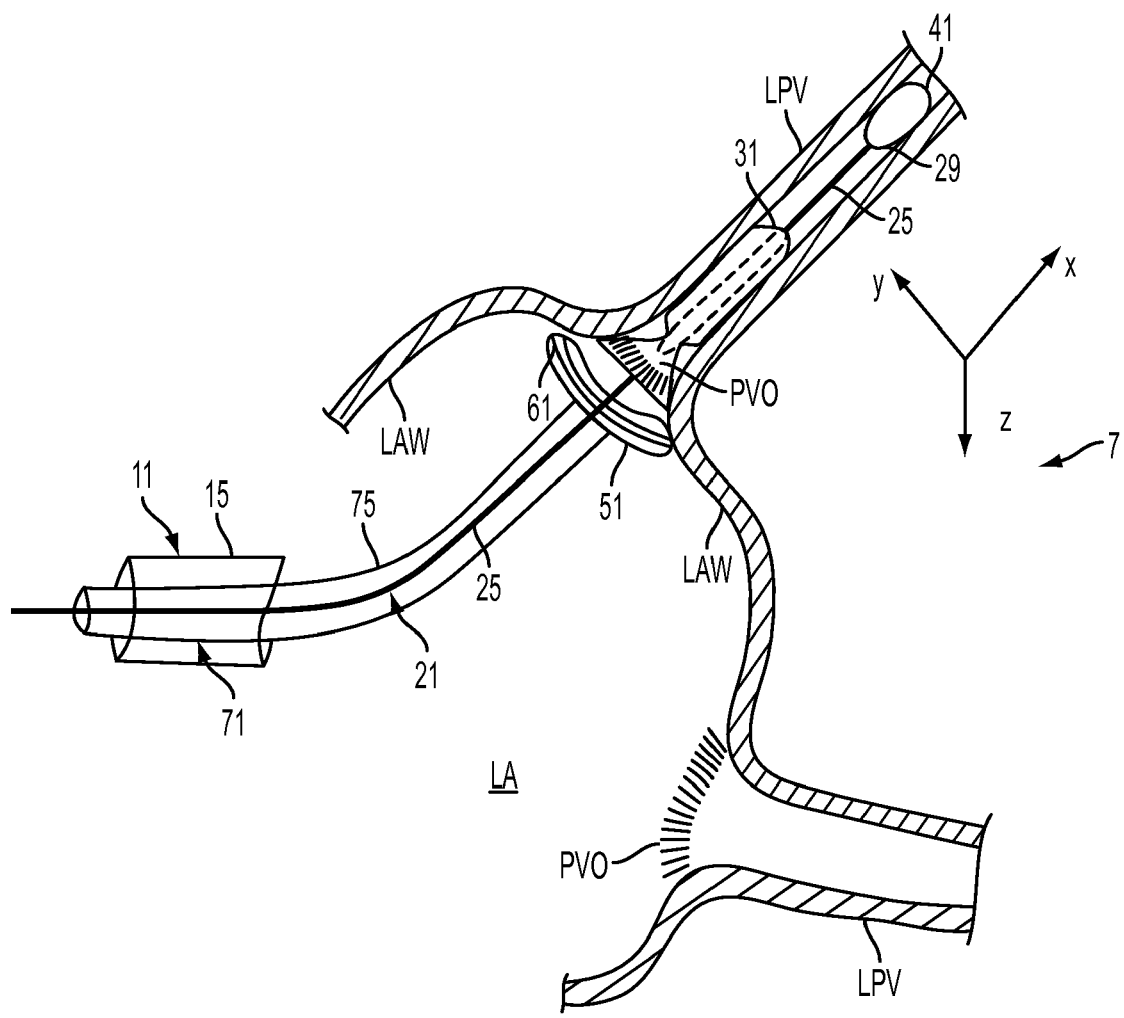

Next, referring to FIG. 12(A) and FIG. 12(B), FIG. 12(A) and FIG. 12(B) schematically illustrate the use of an ablation assembly within a heart wherein the another embodiment of centering/alignment balloon 31 is shown in the non-deployed (restricted/closed) state and the deployed (opened/expanded) state, respectively. As shown in FIG. 12(A), the tip balloon 41 is disposed inside the LPV and the interface member 51 and centering/alignment balloon 31 (deflated/restricted) may be advanced at or proximal to at the PV and/or PVO. As shown in FIG. 12(B), the centering/alignment balloon 31 may be positioned and inflated/expanded enabling the actuator element 61 (e.g., ring or circuit) to create a coaxial alignment with the pulmonary vein (PV) and/or pulmonary vein ostium (PVO); and thus enabling a symmetric ablation line/region (not shown) with the pulmonary vein (PV) and/or pulmonary vein ostium (PVO), i.e., the distance from the ablation line/region to the pulmonary vein ostium (PVO) does not vary. Accordingly, an ablated region or portion is created that circumscribes the PV and/or PVO as desired or required.

Figure 13A:
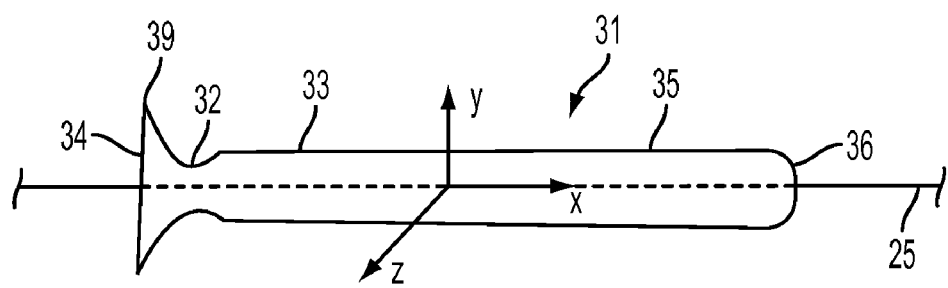
FIGS. 13(A) and 13(B) illustrate a perspective view of an embodiment of the present centering/alignment balloon as shown in the deflated (restricted/closed) state and the inflated (opened/expanded) state, respectively.
Figure 13B:
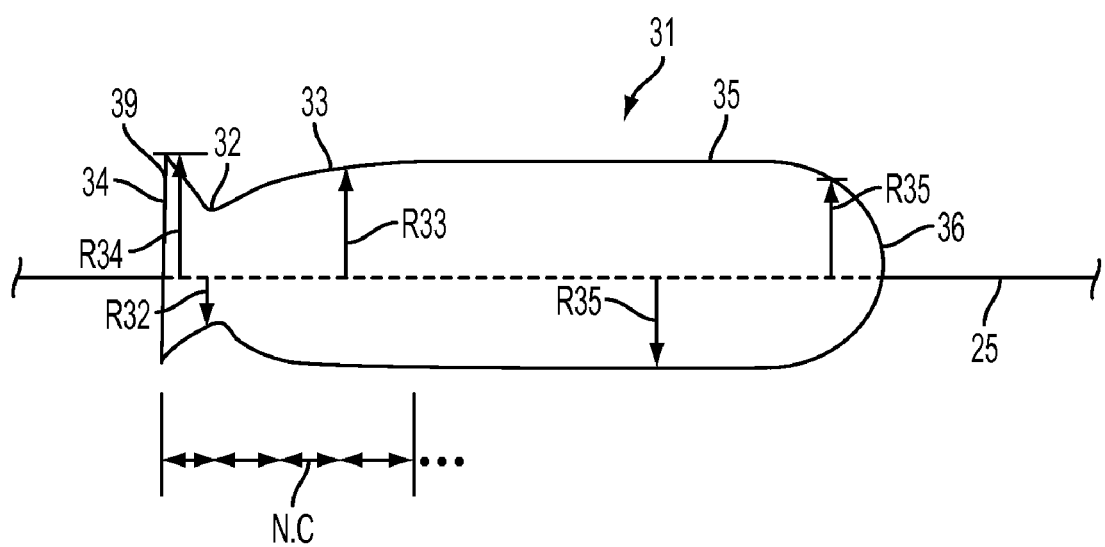

Turning to FIGS. 13(A) and 13(B), FIGS. 13(A) and 13(B) illustrate a perspective view of the present centering/alignment balloon 31 of FIG. 12 in the deflated (restricted/closed) state and inflated (opened/expanded) state, respectively. The centering/alignment balloon 31 includes a distal end 36, distal portion 35, proximal end 34 and proximal portion 33, having a desired/required radius R33 that may vary along its continuum. Additionally, the centering/alignment balloon 31 includes a neck 32 and/or flair 39. At least a portion of the proximal portion 33 includes a coaxial alignment element such as a non-compliant portion, referenced as NC, which may comprise a non-compliant material or structure in whole or in part. The NC of the balloon 31 can be a variety of lengths extending from or proximity thereto the proximal end 34 of the balloon 31 as desired/required being "x" distance distal from the proximal end 34 (or proximally thereto) of the balloon 31. Moreover, any portion of the NC of the balloon can have wide variety of potential shapes. For instance, it should be appreciated that the NC of the centering/alignment balloon 31 may be contoured in any desired/required shape in the longitudinal direction (x-plane) or radial direction (y and z planes) or combination thereof to provide the entire geometric spectrum of potential shapes in the x, y and z planes.

As discussed above, NC of the centering/alignment balloon 31 serves to center and/or align the guide wire 25 in the pulmonary vein (PV) and/or pulmonary vein ostium (PVO) so that the interface member 51 is coaxially aligned with the pulmonary vein ostium (PVO) to provide optimal coaxial alignment with the pulmonary vein ostium (PVO). The remaining portion of the centering/alignment balloon 31 that is not the NC may be designed to have a compliance greater than the compliance of the pulmonary vein (PV) and/or pulmonary vein ostium (PVO) so as to prevent rupture of the pulmonary vein (PV) and/or pulmonary vein ostium (PVO) from the forces exerted by an inflated balloon 31 (or compartment).

Further, the high compliance of the remaining portions/walls (i.e., portions other than the NC) of the centering/alignment balloon 31 provides additional aspects/functions. For instance the high compliance walls of the balloon provide an anchoring mechanism enabled by a large surface area and hydrostatic forces as opposed to pressure. In one approach, the high compliance walls of the centering/alignment balloon 31 (or inflatable compartment) may be comprised of a material that will be non-covalently chemically attractive to the endothelia surface. For instance, the material may provide for hydrophilic interaction, hydrostatic forces, hydrophobic interaction and/or molecular flash atomic polaric forces.

Still referring to FIGS. 12-13, the flair 39 may be in contact with the PVO and/or the left atrium (LA) wall (LAW). In an embodiment, the maximal diameter of the flair 39 would be less than the interface member 51 and/or ablation element 61 so that the interface member 51 and/or ablation element 61 can contact the left atrial tissue, such as the LAW. It should be appreciated that the flair 39 of the centering/alignment balloon 31 may be contoured in any desired/required shape in the longitudinal direction (x-plane) or radial direction (y and z planes) or combination thereof to provide the entire geometric spectrum of potential shapes in the x, y and z planes. For example, the shape may be bell-shaped, olive shaped, hemispherical shaped, ellipsoid shaped or multifaceted shaped, cone shaped, oval shaped, etc.

Still referring to FIGS. 13(A) and 13(B), it should be appreciated that the maximal diameter of portions the radius of the NC (designated as 'RNC') of the centering/alignment balloon 31 that may be disposed inside the LPV is equal to the diameter of the radius of the PV (designated as 'radPV') minus y or z (in the radial direction).

In the various embodiments, any of the balloons discussed herein may include separate inflation devices corresponding to separate balloons in x, y and z planes for the desired effect of shape manipulation. These separate balloons could be covered by a covering balloon material (e.g., outer membrane) or alternatively left bare or alternatively inflated to a pre-formed shape with only size manipulability.

Further advantages of balloon inflation devices discussed herein would be operator control of x, y and z planes of the balloons thus enabling manipulation of shape as well as size in all planes to optimally and as atraumatically as possible intubate variably shaped and sized vasculature space.

It should be appreciated that the balloons 31, 41 (as well as any additional balloons referenced herein) discussed herein may be single compartment balloons, balloons with multiple compartments, multiples balloons or any inflation devices required for separate manipulation of x, y and z planes with a larger covering balloon or balloon like material or membrane covering the three x, y and z plane balloons. This would enable more detailed and/or variable shape changes. Alternatively a "covering" balloon (e.g., outer membrane) could be optional and/or alternatively a balloon could have a pre-formed shape with only size of the balloon being able to be controlled by the operator. Size of the balloons could be a function of balloon material compliance and inflation pressure.

Further, it should be appreciated that the shape of the balloons may be may be semi-elliptical, as well as semi-spherical, hemispherical, semi-oval, partly rounded or partly olive.

The various embodiments of the present invention guide wire system and related method thereof as discussed throughout this document may be implemented with commercially available catheter devices and its components and systems, as well as the catheter device and its components and systems disclosed in PCT Application No. PCT/US2005/037031, filed Oct. 14, 2005, entitled "Vasculature Catheter Device and Related Method of Using the Same," U.S. application Ser. No. 10/577,118, filed Apr. 26, 2006, entitled "Vasculature Catheter Device and Related Method of Using the Same," U.S. application Ser. No. 11/592,560, filed Nov. 3, 2006, entitled "Expandable Component Guide Wire System and Related Method of Using the Same," and PCT Application No. PCT/US2006/043066, filed Nov. 3, 2006, entitled "Expandable Component Guide Wire System and Related Method of Using the Same," of which are hereby incorporated by reference herein in their entirety.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

I claim:

1. A tissue ablation system for treating atrial arrhythmia by ablating a circumferential region of tissue at a location where a pulmonary vein (PV) extends from an atrium of a heart of a subject, said system comprising:

a guide catheter comprising a shaft having a proximal portion and a distal portion;

a guide wire disposed in said guide catheter shaft having a proximal portion, distal portion and distal tip, said guide wire adapted to travel through said guide catheter to be inserted into the atrium;

an interface member disposed on said guide wire;

a first balloon disposed on said guidewire distally beyond said interface member; said first balloon adapted to center or align said guide wire in the pulmonary vein (PV) and/or its pulmonary vein ostium (PVO) so that the interface member is coaxially aligned with the pulmonary vein ostium (PVO) to provide optimal coaxial alignment with the pulmonary vein ostium (PVO);

an actuator element disposed on said interface member; and said interface member to be positioned to center and/or align said guide wire, said interface member and/or actuator element in the pulmonary vein (PV) and/or it's pulmonary vein ostium (PVO) so that the interface member and/or actuator element is coaxially aligned with the pulmonary vein ostium (PVO) to provide optimal coaxial alignment with the pulmonary vein ostium (PVO).

2. The system of claim 1, wherein said first balloon having a compliance greater than the compliance of the pulmonary vein (PV) and/or the pulmonary vein ostium (PVO) so as to prevent rupture of the pulmonary vein (PV) and/or pulmonary vein ostium (PVO) from the forces exerted by an said first balloon when inflated.

3. The system of claim 1, wherein at least portions of said interface member having a compliance greater than the compliance of the pulmonary vein (PV) and/or pulmonary vein ostium (PVO) so as to prevent rupture of the pulmonary vein (PV) and/or pulmonary vein ostium (PVO) from the forces exerted by said interface member.

4. The system of claim 1, wherein said first balloon adapted to provide an anchoring function to provide leverage to push said interface member against the wall of the atrium for optimum contact to assure success.

5. The system of claim 4, wherein said anchoring function is enabled by surface area and/or hydrostatic forces.

6. The system of claim 4, wherein said anchoring function is enabled by pressure.

7. The system of claim 4, wherein said first balloon is comprised of a material that will be non-covalently chemically attractive to the endothelia surface.

8. The system of claim 1, wherein the material of said first balloon may provide for hydrophilic interaction, hydrostatic forces, hydrophobic interaction and/or molecular flash atomic polaric forces.

9. The system of claim 1, wherein said ablation element is a ring or circuit.

10. The system of claim 1, wherein said first balloon may be have a shape or inflated to a shape that may be contoured in any desired/required shape in the longitudinal (x-plane) or radial direction (y and z planes) or combination thereof to provide the entire geometric spectrum of potential shapes in the x, y and z planes.

11. The system of claim 1, wherein said first balloon having a portion that is non-compliant.

12. The system of claim 11, wherein said non-compliant portion comprising at least one of: rib-like structure, ring-like structure, doughnut-like structure, or rim-like structure when inflated.

13. The system of claim 11, wherein said non-compliant portion serves to improve the centering and/or aligning of the guide wire in the pulmonary vein (PV) and/or its pulmonary vein ostium (PVO) so that said interface member is coaxially aligned with the pulmonary vein ostium (PVO) to provide optimal coaxial alignment with the pulmonary vein ostium (PVO).

14. The system of claim 11, wherein said non-compliant portion is sized to a radius of the sized to a radius of the of the pulmonary vein ostium (PVO) minus a clearance distance as required or desired.

15. The system of claim 14, wherein said non-compliant portion is sized according to anatomical and procedural requirements.

16. The system of claim 11, wherein said non-compliant portion is integral, removably coupled, or fixed together with the remaining portion of said first balloon that is not said non-compliant portion of said first balloon.

17. The system of claim 11, wherein said non-compliant portion may be part of the inflation material of said first balloon or may not be part of the inflation function of said first balloon.

18. The system of claim 11, wherein said non-compliant portion being located on the proximal portion said first balloon.

19. The system of claim 11, wherein said wherein said non-compliant portion being a spiral structure, x-shaped structure, zigzag structure, or grid-like structure.

20. The system of claim 1, further comprising a non-traumatic tip compartment, said non-traumatic compartment disposed at or proximal to said distal wire tip.

21. The system of claim 20, wherein said non-traumatic compartment comprises an inflatable balloon or compartment, as well as a J-tip, non-traumatic tip, or other type of non-traumatic tip.

22. The system of claim 20, wherein said first balloon and/or non-traumatic tip compartment may have at least one the following shapes: olive, bulbous, rounded, spherical, hemispherical, conical, oval, tapered, beveled, chamfered, graduated and/or multi-faceted, or any combination thereof.

23. The system of claim 20, wherein said first balloon and/or non-traumatic tip compartment may have has at least one the following shapes: semi-elliptical, semi-spherical, hemispherical, semi-oval, partly rounded or partly olive, or any combination thereof.

24. The system of claim 20, wherein said first balloon and/or non-traumatic tip compartment may have a size that is manipulated by varying the compliance of the material and inflation pressure.

25. The system of claim 1, and wherein a segment of said distal portion of said guide wire that is located distally beyond said interface member provides a distal extension.

26. The system of claim 1, wherein said actuator element delivers an energy source to the intended region of tissue.

27. The system of claim 26, wherein said energy source creates an ablated region or portion that circumscribes the PV and/or PVO as desired or required.

28. The system of claim 27, wherein the difference between radius of the actuator element, designated as 'RAE,' and the radius of the PVO, designated as 'RPVO,' equals the distance as 'd' defining the ablation region.

29. The system of claim 1, wherein a lumen of said guide wire may be utilized for accommodating a communication channel or wire for delivering energy from an ablation actuator to the ablation element of said interface member.

30. The system of claim 1, wherein a lumen of said guide wire may be utilized for inflating said first balloon or delivering inert gas, radiographic contrast, or fluid.

31. The system of claim 1, wherein said guide wire implements a multi-lumen guide wire structure.

32. The system of claim 1, wherein said interface member comprises a plurality of panels folded or collapsed over causing said interface member to be in a deflated or restricted state and unfolded or un-collapsed causing said interface member to be in an inflated or expanded state.

33. The system of claim 32, wherein said plurality of panels may be individual segments or one continuous surface.

34. The system of claim 32, wherein said interface member in said inflated or expanded state has shape comprising: bell-shaped, olive shaped, hemispherical shaped, ellipsoid shaped or multifaceted shaped, cone shaped, or oval shaped.

35. The system of claim 32, wherein said interface member in said inflated or expanded state has its wall that that may be angled a variety of degrees relative to the longitudinal axis of said guide wire at the location of said interface member to accommodate successful ablation of the tissue region.

36. The system of claim 35, wherein said actuator element has a circuit that runs along the longitudinal axis and radially across to the rim of said interface member.

37. The system of claim 35, wherein said actuator element has a circuit that runs along the wall of said interface member toward the rim of said interface member.

38. The system of claim 35, wherein said actuator element has a circuit that is wireless or hard wired.

39. The system of claim 32, wherein said interface member may be compressible to pass-through a sheath to pass through a sheath in a compressed state and expandable after it passes through the sheath.

40. The system of claim 1, further comprising:
a delivery catheter comprising a shaft having a proximal portion and a distal portion; said delivery catheter travels coaxially through said guide catheter, said guide wire travels coaxially through said delivery catheter;
a proximal hub slidably disposed on said delivery catheter at distal portion of said delivery catheter, said proximal hub having a plurality of proximal spokes attached to said proximal hub; and
a distal huh slidably disposed on said delivery catheter and in contact with said proximal hub, said distal hub having a plurality of distal spokes attached to said distal huh;
wherein when a force is applied in a distal direction to said proximal hub:
said proximal hub is pushed as close to the distal hub as possible, or as desired, thereby causing the proximal and distal set of spokes to be deployed and flare outward relative to the longitudinal axis of said proximal hub and distal hub, and
wherein when a force is applied in a proximal direction to said proximal hub:
said proximal hub pulled away or slid away from said distal hub as much as possible, or as desired, thereby causing the proximal and distal set of spokes to be in a to collapse in a non-deployed state.

41. The system of claim 40, wherein said ablation element may be folded, collapsed, or arranged on the under side of the proximal spokes and/or distal spokes.

42. The system of claim 41, wherein while said proximal and distal spokes are in a collapsed state the ablation element wire may be folded in an accordion-like manner and will not be visible.

43. The system of claim 41, wherein while said proximal and distal spokes are in the deployed or flared state the ablation element wire is caused to unfold or release to form a ring or rim; and while said ablation element is energized said actuator element ablates the tissue region.

44. The system of claim 1, wherein said actuator element and said interface member circumscribes said guide wire.

45. A tissue ablation system for treating atrial arrhythmia by ablating a circumferential region of tissue at a location where a pulmonary vein (PV) extends from an atrium of a heart of a subject, said system comprising:
a guide catheter comprising a shaft having a proximal portion and a distal portion;
a guide wire disposed in said guide catheter shaft having a proximal portion, distal portion and distal tip, said guide wire adapted to travel through said guide catheter to be inserted into the atrium;
an interface member disposed on said guide wire;
a first balloon disposed on said guidewire distally beyond said interface member, said first balloon comprises distal end, distal portion, proximal end and proximal portion;
a non-compliance portion being located on said proximal portion of said first balloon, said proximal portion having a desired/required radius that may vary along its continuum;
said non-compliance portion is adapted to center or align said guide wire in the pulmonary vein (PV) and/or its pulmonary vein ostium (PVO) so that the interface member is coaxially aligned with the pulmonary vein ostium (PVO) to provide optimal coaxial alignment with the pulmonary vein ostium (PVO); and
an actuator element disposed on said interface member.

46. The system of claim 45, wherein said interface member to be positioned to center and/or align said guide wire, said interface member and/or actuator element in the pulmonary vein (PV) and/or it's pulmonary vein ostium (PVO) so that the interface member and/or actuator element is coaxially aligned with the pulmonary vein ostium (PVO) to provide optimal coaxial alignment with the pulmonary vein ostium (PVO).

47. The system of claim 45, wherein the non-compliance portion can be a variety of lengths extending from or proximity thereto the proximal end of said first balloon as desired, or required being "x" distance distal from said proximal end of said first balloon.

48. The system of claim 45, wherein said non-compliance portion may have a shape or inflated to a shape that may be contoured in any desired/required shape in the longitudinal (x-plane) or radial direction (y and z planes) or combination thereof to provide the entire geometric spectrum of potential shapes in the x, y and z planes.

49. The system of claim 45, wherein said non-compliance portion may have at least one the following shapes: olive, bulbous, rounded, spherical, hemispherical, conical, oval, tapered, beveled, chamfered, graduated and/or multi-faceted, or any combination thereof.

50. The system of claim 45, wherein said non-compliance portion may have has at least one the following shapes: semi-elliptical, semi-spherical, hemispherical, semi-oval, partly rounded or partly olive, or any combination thereof.

51. The system of claim 45, wherein at least a portion other than said non-compliant portion is designated as high compliance portion; and
said high compliance portion having compliance greater than said non-compliance portion so as to prevent rupture of the pulmonary vein (PV) and/or pulmonary vein ostium (PVO) from the forces exerted by said first balloon when inflated.

52. The system of claim 51, wherein a wall of said high compliance portion of said first balloon provides an anchoring function.

53. The system of claim 52, wherein said anchoring function is enabled by surface area and/or hydrostatic forces.

54. The system of claim 52, wherein said anchoring function is enabled by pressure.

55. The system of claim 52, wherein said wall of said high compliance portion comprises of a material that will be non-covalently chemically attractive to the endothelia surface.

56. The system of claim 52, wherein the wall of said high compliance portion comprises of a material that provides for hydrophilic interaction, hydrostatic forces, hydrophobic interaction and/or molecular flash atomic polaric forces.

57. The system of claim 45, wherein said first balloon 31 is positioned and inflated/expanded enabling said actuator element 61 to create a coaxial alignment with the pulmonary vein (PV) and/or pulmonary vein ostium (PVO) enabling a symmetric ablation region of the tissue of the pulmonary vein (PV) and/or pulmonary vein ostium (PVO).

58. The system of claim 57, wherein the radial distance from the actuator element radial to the pulmonary vein ostium (PVO) does not vary.

59. The system of claim 57, wherein an ablated region or portion of the tissue is created that circumscribes the PV and/or PVO as desired or required.

60. The system of claim 57, wherein the maximal diameter of the radius of the non-conformance portion of said first balloon is equal to the diameter of the radius of the PV minus 'y' or 'z', wherein 'y' or 'z' is in the radial direction.

61. The system of claim 45, wherein at least a portion of said proximal portion of said first balloon comprises a neck or flair.

62. The system of claim 45, wherein said actuator element and said interface member circumscribes said guide wire.

* * * * *